US012653800B2

(12) United States Patent
Vogel et al.

(10) Patent No.: US 12,653,800 B2
(45) Date of Patent: Jun. 16, 2026

(54) SMALL MOLECULE INHIBITORS OF TLR2 SIGNALING

(71) Applicant: University of Maryland, Baltimore, Baltimore, MD (US)

(72) Inventors: Stefanie N Vogel, Columbia, MD (US); Alexander MacKerell, Jr., Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 1517 days.

(21) Appl. No.: 15/564,734

(22) PCT Filed: Apr. 6, 2016

(86) PCT No.: PCT/US2016/026147
§ 371 (c)(1),
(2) Date: Oct. 5, 2017

(87) PCT Pub. No.: WO2016/164414
PCT Pub. Date: Oct. 13, 2016

(65) Prior Publication Data
US 2018/0110746 A1 Apr. 26, 2018

Related U.S. Application Data

(60) Provisional application No. 62/143,324, filed on Apr. 6, 2015.

(51) Int. Cl.
*A61K 31/196* (2006.01)
*A61K 31/11* (2006.01)
(Continued)

(52) U.S. Cl.
CPC ............ *A61K 31/196* (2013.01); *A61K 31/11* (2013.01); *A61K 31/136* (2013.01); *A61K 31/18* (2013.01);
(Continued)

(58) Field of Classification Search
CPC .............................. A61K 31/196; A61K 31/11
See application file for complete search history.

(56) References Cited

U.S. PATENT DOCUMENTS 5,668,182 A * 9/1997 Abraham .............. A61K 31/11 514/532
6,251,927 B1 6/2001 Lai
(Continued)

FOREIGN PATENT DOCUMENTS

EP 1136080 A2 9/2001
WO WO-2005030189 A1 * 4/2005 ............ A61K 31/05
(Continued)

OTHER PUBLICATIONS

Reagan-Shaw et al., FASEBJ vol. 22 pp. 659-661 Published 2007 (Year: 2007).*
(Continued)

*Primary Examiner* — George W Kosturko
(74) *Attorney, Agent, or Firm* — Nevrivy Patent Law Group P.L.L.C.

(57) ABSTRACT

The present invention is drawn to therapeutics and methods of inhibiting signaling by TLR2. The invention provides a method of treating an inflammatory disease or condition in a subject comprising administering to the subject a therapeutically effective amount of a compound of the invention or salt, solvate, hydrate, prodrug, metabolite, or combination thereof.

19 Claims, 14 Drawing Sheets

(51) Int. Cl.

| | |
|---|---|
| ***A61K 31/136*** | (2006.01) |
| ***A61K 31/18*** | (2006.01) |
| ***A61K 31/381*** | (2006.01) |
| ***A61K 31/437*** | (2006.01) |
| ***A61K 31/4406*** | (2006.01) |
| ***A61K 31/4439*** | (2006.01) |
| ***A61K 31/513*** | (2006.01) |
| ***A61K 31/517*** | (2006.01) |
| ***A61K 31/519*** | (2006.01) |
| ***A61K 31/5355*** | (2006.01) |
| ***A61K 31/5377*** | (2006.01) |
| ***A61K 45/06*** | (2006.01) |
| ***A61P 29/00*** | (2006.01) |

(52) U.S. Cl.

CPC .......... *A61K 31/381* (2013.01); *A61K 31/437* (2013.01); *A61K 31/4406* (2013.01); *A61K 31/4439* (2013.01); *A61K 31/513* (2013.01); *A61K 31/517* (2013.01); *A61K 31/519* (2013.01); *A61K 31/5355* (2013.01); *A61K 31/5377* (2013.01); *A61K 45/06* (2013.01); *A61P 29/00* (2018.01)

(56) References Cited

U.S. PATENT DOCUMENTS

| | | | | |
|---|---|---|---|---|
| 2009/0285890 | A1* | 11/2009 | Van Den Plas ........ | A01N 31/16 424/484 |
| 2010/0233168 | A1 | 9/2010 | Wanderer | |
| 2014/0336159 | A1 | 11/2014 | Clarke et al. | |

FOREIGN PATENT DOCUMENTS

| | | | | |
|---|---|---|---|---|
| WO | WO-2009097113 | A2 * | 8/2009 | ........... A61K 31/439 |
| WO | WO-2010053606 | A2 * | 5/2010 | .............. A61P 39/02 |
| WO | 2015048083 | A1 | 4/2015 | |

OTHER PUBLICATIONS

Acute Respiratory Distress Syndome Fact Sheet. American College of Cardiology published 2011. (Year: 2011).*

Caujolle et al (Travaux de la Societe de Pharmacie de Montpellier vol. 14. Published 1954 (abstract provided) (Year: 1954).*

Madrid et al, (J. Chil.Chem. Soc. vol. 58 pp. 1814-1816 published 2013) (Year: 2013).*

Arslan et al., Treatment With OPN-305, a Humanized Anti-Toll-Like Receptor-2 Antibody, Reduces Myocardial Ischemia/Reperfusion Injury in Pigs, Circulation Cardiovascular interventions, 5:279-287 (2012).

Beaudry et al., Pharmacokinetics of Vanillin and its Effects on Mechanical Hypersensitivity in a Rat Model of Neuropathic Pain, Phytotherapy research, 4:525-530 (2010).

Brooks et al., CHARMM: The Biomolecular Simulation Program, Journal of computational chemistry, 30:1545-1614 (2009).

Brown et al., Binding specificity of Toll-like receptor cytoplasmic domains, European journal of immunology, 36:742-753 (2006).

Castoldi et al., TLR2, TLR4 and the MYD88 Signaling Pathway Are Crucial for Neutrophil Migration in Acute Kidney Injury Induced by Sepsis, PloS one, 7:e37584 (2012).

Cheng et al., Discovery of Small-Molecule Inhibitors of the TLR1/TLR2 Complex, Angewandte Chemie, 51:12246-12249 (2012).

Cole et al., Immunologic Consequences of Francisella tularensis Live Vaccine Strain Infection: Role of the Innate Immune Response in Infection and Immunity, Journal of immunology, 176:6888-6899 (2006).

Cole et al., Toll-Like Receptor 2-Mediated Signaling Requirements for Francisella tularensis Live Vaccine Strain Infection of Murine Macrophages, Infection and immunity, 75:4127-4137 (2007).

Gautam et al., Structural and Functional Evidence for the Role of the TLR2 DD Loop in TLR1/TLR2 Heterodimerization and Signaling, The Journal of biological chemistry, 281:30132-30142 (2006).

Han et al., Pneumococcal Lipoteichoic Acid (LTA) Is Not as Potent as Staphylococcal LTA in Stimulating Toll-Like Receptor 2, Infection & Immunity, 71:5541-5548 (2003).

Hancock et al., Identification of Novel Extracellular Signal-Regulated Kinase Docking Domain Inhibitors, Journal of medicinal chemistry, 48:4586-4595 (2005).

Katz et al., Toll-Like Receptor 2 Is Required for Inflammatory Responses to Francisella tularensis LVS, Infection and Immunity, 74:2809-2816 (2006).

Kumar et al., Pathogen Recognition by the Innate Immune System, International reviews of immunology, 30:16-34 (2011).

Kwon et al., Inflammation-Responsive Antioxidant Nanoparticles Based on a Polymeric Prodrug of Vanillin, Biomacromolecules, 14:1618-1626 (2013).

MacKerell et al., Extending the Treatment of Backbone Energetics in Protein Force Fields: Limitations of Gas—Phase Quantum Mechanics in Reproducing Protein Conformational Distributions in Molecular Dynamics Simulations, J. Comp. Chem., 25:1400-1415 (2004).

MacKerell et al., Improved Treatment of the Protein Backbone in Empirical Force Fields, J. Am. Chem. Soc., 126:698-699 (2004).

Meng et al., Antagonistic antibody prevents toll-like receptor 2-driven lethal shock-like syndromes, The Journal of clinical investigation, 113:1473-1481 (2004).

Schroder et al., Lipoteichoic Acid (LTA) of *Streptococcus pneumoniae* and *Staphylococcus aureus* Activates Immune Cells via Toll-like Receptor (TLR)-2, Lipopolysaccharide-binding Protein (LBP), and CD14, whereas TLR-4 and MD-2 Are Not Involved, The Journal of biological chemistry, 278:15587-15594 (2003).

Travassos et al., Toll-like receptor 2-dependent bacterial sensing does not occur via peptidoglycan recognition, EMBO reports, 5:1000-1006 (2004).

Xu et al., Structural basis for signal transduction by the Toll/interleukin-1 receptor domains, Nature, 408:111-115 (2000).

International Search Report from International Appl. No. PCT/US2016/026147, mailed on Jul. 8, 2016.

Mistry et al., Inhibition of TLR2 signaling by small molecule inhibitors targeting a pocket within the TLR2 TIR domain, Proceedings of the National Academy of Sciences, 112:5455-5460 (2015).

Official Communication from European Appl. No. 16777169.0, mailed on Nov. 23, 2018.

Extended Search Report from European Appl. No.16777169.0, mailed on Nov. 7, 2018.

* cited by examiner

SMALL MOLECULE INHIBITORS OF TLR2 SIGNALING

CROSS-REFERENCE TO RELATED APPLICATIONS

This application claims the benefit of U.S. Provisional Appl. No.: 62/143,324, filed Apr. 6, 2015. The content of the aforementioned application is relied upon and is incorporated by reference in its entirety.

STATEMENT OF FEDERALLY SPONSORED RESEARCH AND DEVELOPMENT

This invention was made with government support under Grant Number AI018797 awarded by the National Institutes of Health. The government has certain rights in the invention.

FIELD OF THE INVENTION

The field of this invention generally relates to the fields of medicine and immunology. In particular, the field of the invention relates to molecules which are inhibitors of Toll-like Receptor 2 (TLR2) signaling and play a role in inflammatory diseases.

BACKGROUND

Toll-like receptors (TLRs) are a family of transmembrane innate immune molecules that play a key role in the detection of microbial and self-ligands released from damaged cells. At their C-termini, Toll/Interleukin-1 receptor (TIR) domains dimerize upon ligand binding and initiate a signaling cascade that leads to upregulation of inflammatory cytokines. Over-exuberant signaling leads to a "cytokine storm," causing extensive tissue damage that can be fatal. The ability to block TLR signaling may ameliorate such a scenario.

TLRs are type I transmembrane receptors that detect conserved "pathogen-associated molecular patterns" (PAMPs) from microbes, as well as host-derived "danger-associated molecular patterns" (DAMPs) (Medzhitov R (2001) *Nature reviews. Immunology* 1(2):135-145). TLR2 heterodimerizes with TLR6 or TLR1 to recognize diacyl lipopeptides or triacyl lipopeptides, respectively (Takeuchi O, et al. (2001) *International immunology* 13(7):933-940; Takeuchi O, et al. (2002) *Journal of immunology* 169(1):10-14), present in Gram-positive and Gram-negative bacteria (Cole L E, et al. (2006) *Journal of immunology* 176(11):6888-6899; Cole L E, et al. (2007) *Infection and immunity* 75(8):4127-4137; Medina E A, Morris I R, & Berton M T (2010) *Journal of immunology* 185(12):7562-7572; Raoust E, et al. (2009) *PloS one* 4(10):e7259; Schroder N W, et al. (2003) *The Journal of biological chemistry* 278(18):15587-15594; Yoshimura A, et al. (1999) *Journal of immunology* 163(1):1-5).

Ligand engagement of TLR2/TLR1 or TLR2/TL6 activates the MyD88-dependent pathway, i.e., nuclear translocation of NF-κβ and activation of MAPKs, resulting in production of proinflammatory cytokines (Kumar H, Kawai T, & Akira S (2011) *International reviews of immunology* 30(1):16-34). Dysregulated TLR2 signaling has been implicated in numerous diseases (e.g., sepsis, atherosclerosis, tumor metastasis, and ischemia/reperfusion injury) (Castoldi A, et al. (2012) *PloS one* 7(5):e37584; Leemans J C, et al. (2005) 115(10):2894-2903; Mullick A E, Tobias P S, & Curtiss L K (2005) *The Journal of clinical investigation* 115(11):3149-3156; Yang H Z, et al. (2009) *PloS one* 4(8):e6520). Several inhibitors of TLR2 signaling have been developed (Arslan F, et al. (2012) *Circulation. Cardiovascular interventions* 5(2):279-287; Cheng K, Wang X, Zhang S, & Yin H (2012) *Angewandte Chemie* 51(49):12246-12249; Meng G, et al. (2004) *The Journal of clinical investigation* 113(10):1473-1481; Murgueitio M S, et al. (2014) *ChemMedChem* 9(4):813-822), yet none is licensed for human use. A better understanding of the TIR domain interactions involved in TLR2 signaling could lead to novel therapeutic agents.

Both TLRs and adapter proteins contain a cytoplasmic TIR domain that mediates homotypic and heterotypic interactions during TLR signaling (Akira S, Uematsu S, & Takeuchi O (2006) *Cell* 124(4):783-801). Two adapter proteins implicated in TLR2 signaling are MyD88 and TIRAP (Mal). A conserved proline (e.g., P681 in hTLR2, P712 in mTLR4, P674 in hTLR10, and P804 in mTLR11) within the BB loop of almost all TIR domains is critical for signaling (Brown V, et al. (2006) *European journal of immunology* 36(3):742-753; Hasan U, et al. (2005) *Journal of immunology* 174(5):2942-2950; Poltorak A, et al. (1998) *Science* 282(5396):2085-2088; Qureshi S T, et al. (1999) *The Journal of experimental medicine* 189(4):615-625; Underhill D M, et al. (1999) *Nature* 401(6755):811-815; Underhill D M, et al. (1999) *Proceedings of the National Academy of Sciences of the United States of America* 96(25):14459-14463; Xu Y, et al. (2000) *Nature* 408(6808):111-115; Zhang D, et al. (2004) *Science* 303(5663):1522-1526). More importantly, the BB loop P681H mutation in human TLR2 abolished recruitment of MyD88 and signaling (Brown V, et al. (2006) *European journal of immunology* 36(3):742-753; Xu Y, et al. (2000) *Nature* 408(6808):111-115). The BB loop within the TLR2 TIR domain appears to be an ideal target for attenuation of TLR2 signaling.

This background information is provided for informational purposes only. No admission is necessarily intended, nor should it be construed, that any of the preceding information constitutes prior art against the present invention.

SUMMARY

It is to be understood that both the foregoing general description of the embodiments and the following detailed description are exemplary, and thus do not restrict the scope of the embodiments.

Excess TLR2 signaling has been implicated in numerous inflammatory diseases, yet there is no TLR2 inhibitor licensed for human use. Using Computer-Aided Drug Design (CADD), C29, as well as a derivative, ortho-vanillin (hereinafter sometimes referred to as C29L), were identified that inhibit TLR2 signaling in vitro and in vivo. The present findings also revealed unexpected differences between TLR2/1 and TLR2/6 signaling in mice vs. humans. Importantly, the data provide proof of principle that the CADD-targeted BB loop pocket residues are critical for TLR2 signaling and may be targeted therapeutically.

Toll-like receptor (TLR) signaling is initiated by dimerization of intracellular Toll-Interleukin-1 receptor resistance (TIR) domains. For all TLRs, except TLR3, recruitment of the adapter, MyD88, to TLR TIR domains results in downstream signaling, culminating in proinflammatory cytokine production. Therefore, blocking TLR TIR dimerization may ameliorate TLR2-mediated hyperinflammatory states. The BB loop within the TLR TIR domain is critical for mediating certain protein-protein interactions.

Examination of the human TLR2 TIR domain crystal structure revealed a pocket adjacent to the highly conserved P681 and G682 BB loop residues. Using Computer-Aided Drug Design (CADD), small molecule inhibitor(s) that would fit within this pocket and, potentially, disrupt TLR2 signaling were sought. In silico screening identified 149 compounds and 20 FDA-approved drugs based on their predicted ability to bind in the BB loop pocket. These were screened in HEK293T-TLR2 transfectants for the ability to inhibit TLR2-mediated IL-8 mRNA. $C_{16}H_{15}NO_4$ ("C29") was identified as a potential TLR2 inhibitor. C29, and its derivative, ortho-vanillin (o-vanillin), inhibited TLR2/1 and TLR2/6 signaling induced by synthetic and bacterial TLR2 agonists in human HEK-TLR2 and THP-1 cells, but only TLR2/1 signaling in murine macrophages. C29 failed to inhibit signaling induced by other TLR agonists and the TNF receptor. Mutagenesis of BB loop pocket residues revealed an indispensable role for TLR2/1, but not TLR2/6 signaling, suggesting divergent roles. Mice treated with o-vanillin exhibited reduced TLR2-induced inflammation. The data provided herein evidences that targeting the BB loop pocket is an effective approach for identification of TLR2 signaling inhibitors.

According to non-limiting example embodiments, in one aspect, the invention provides a method of treating an inflammatory disease or condition in a subject comprising administering to the subject a therapeutically effective amount of a compound selected from the group consisting of C10, C14, C24, C25, C26, C29, C29L, C30, C32, and C33, or salt, solvate, hydrate, prodrug, metabolite, or combination thereof.

In another aspect, the invention provides an anti-inflammatory composition comprising a compound selected from the group consisting of C10, C14, C24, C25, C26, C29, C29L, C30, C32, and C33, or salt, solvate, hydrate, prodrug, metabolite, or combination thereof, and a pharmaceutically acceptable excipient.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

Figure 1:
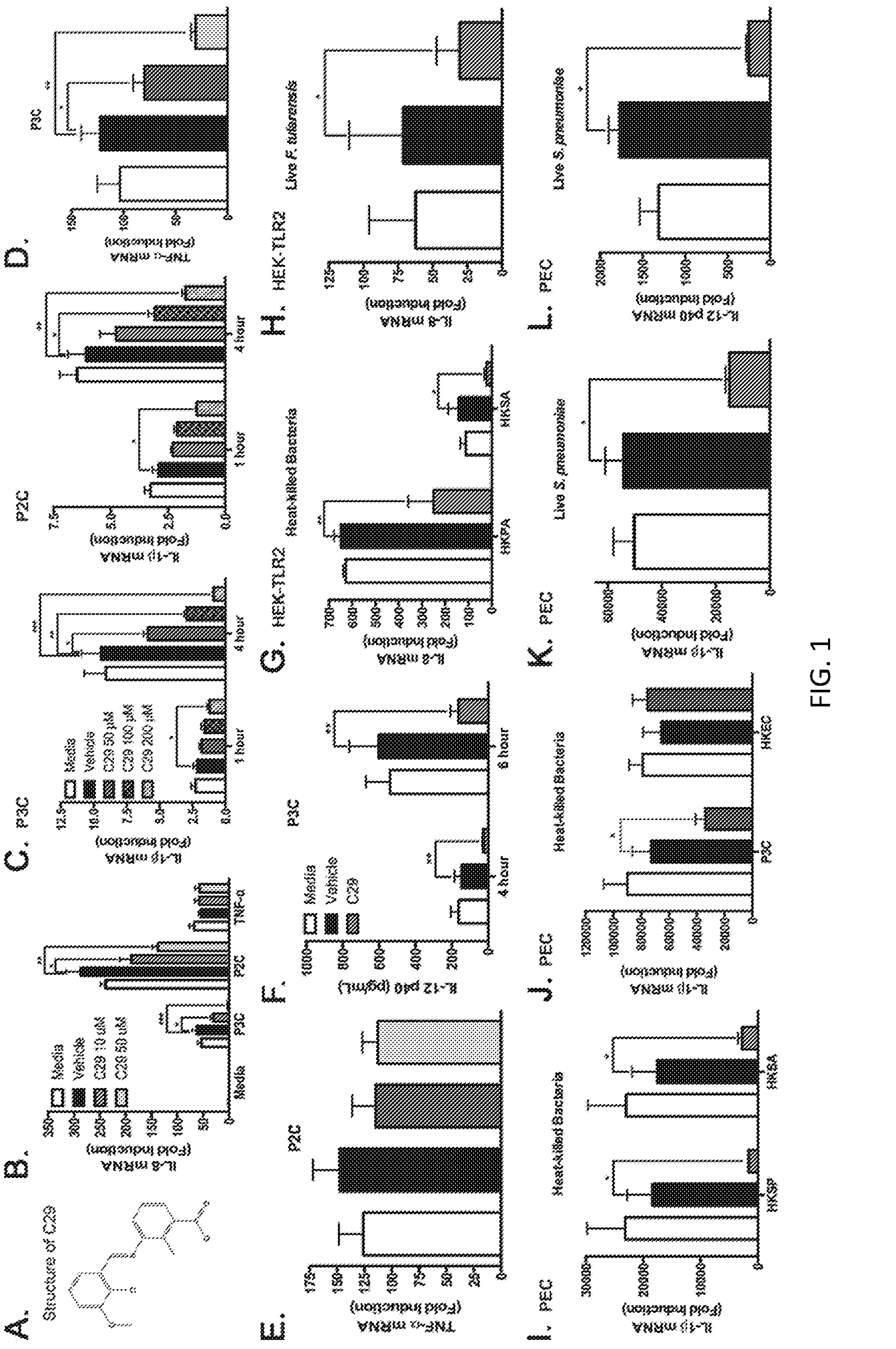
FIG. 1. Differential effect of C29 on gene expression in human cell lines and murine peritoneal macrophages. (A) Structure of C29. (B) Total RNA was extracted from HEK-TLR2 cells pretreated for 1 hr with media, vehicle (65 μM NaOH), or C29 (10 μM or 50 μM) and then stimulated with P3C (200 ng/mL), P2C (200 ng/mL), or hTNF-α (300 ng/mL) for 1 hr in the presence of media, vehicle, or C29. IL-8 mRNA was measured by qRT-PCR and was normalized to the expression of GAPDH housekeeping gene. (C) THP-1 human macrophage-like cell line was plated in the presence of PMA (20 ng/mL) for 24 hrs and washed twice in media. Total RNA was extracted from cell cultures pretreated for 1 hr with media, vehicle (260 μM NaOH), or C29 (50 μM, 100 μM, or 200 μM) and then stimulated with P3C (50 ng/mL) (Left) or P2C (50 ng/mL) (Right) for 1 or 4 hrs in the presence of media, vehicle, or C29. IL-1β mRNA was measured as described in (B). (D, E) Total RNA was extracted from murine peritoneal macrophages that had been pretreated for 1 hr with media (white bars), vehicle (130 μM NaOH) (black bars), or C29 (25 μM (dark gray bars) or 50 μM (light gray bars)) and then stimulated with P3C (50 ng/mL) or P2C (100 ng/mL) for 1 hr in the presence of media, vehicle, or C29. TNF-α mRNA was measured by qRT-PCR and was normalized to the expression of HPRT housekeeping gene. (F) Murine peritoneal macrophages were pretreated for 1 hr with media, vehicle, or C29 (50 μM) and then stimulated with P3C (50 ng/mL) for 4 or 6 hrs in the presence of media, vehicle, or C29. Culture supernatants were analyzed by ELISA for IL-12 p40 protein. (G, H) HEK-TLR2 stable transfectants and (I-L) murine peritoneal macrophages (PEC). Total RNA was extracted from cell cultures pretreated for 1 hr with media, vehicle (65 μM NaOH) or C29 (50 μM) and then stimulated with HKPA (MOI=50), HKSA (MOI=50), HKSP (MOI=50), P3C (50 ng/mL), HKEC (MOI=0.1), live *F. tularensis* LVS (MOI=10) or live *S. pneumoniae* (MOI=0.7) for 4 hrs in the presence of media, vehicle, or C29. RNA was analyzed by qRT-PCR for the expression of the indicated gene products. Quantitative RT-PCR results shown in panels B-E and G-L are the mean±SEM from 2 independent experiments and panel F is the mean±SEM from 3 independent experiments each carried out in duplicate (*, $p \leq 0.05$; , $p \leq 0.01$; *, $p \leq 0.001$).

with interacting loops and helices. The dimeric interfaces of TIR1 and TIR2 involve BB, CD, and DD loops along with either αC or αB helices to mediate dimerization. In contrast, the interface of the TIR6 dimer primarily uses the CD loop, DD loop, and αC helix to mediate dimerization and does not involve the BB loop.

DETAILED DESCRIPTION

The present invention is directed to inhibitors of TLR2 and methods of using such inhibitors.

Visual inspection of the crystal structure of human TLR2 TIR domain revealed a pocket formed by residues on the β-B strand and αB helix that includes the highly conserved proline and glycine residues of the BB loop. It was hypothesized that targeting this pocket with a small molecule might inhibit interaction of TLR2 with MyD88 and, thereby, blunt TLR2 signaling. $C_{16}H_{15}NO_4$ ("C29"), as well as its derivative, o-vanillin, were identified as inhibiting murine and human TLR2 signaling initiated by synthetic and bacterial agonists without cytotoxicity. Interestingly, mutation of the BB loop pocket residues revealed a differential requirement for TLR2/1 vs. TLR2/6 signaling. The data herein indicate that Computer-Aided Drug Design (CADD) is an effective approach for identifying small molecule inhibitors of TLR2 signaling and has the potential to identify inhibitors for other TLR signaling pathways.

Unless otherwise noted, technical terms are used according to conventional usage. Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: A Comprehensive Desk Reference*, published by Wiley, John & Sons, Inc., 1995 (ISBN 0471186341); and other similar technical references.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

In one embodiment, the invention is directed towards a method of treating an inflammatory disease or condition in a subject comprising administering to the subject a therapeutically effective amount of a compound selected from the group consisting of C10, C14, C24, C25, C26, C29, C29L, C30, C32, C33, and combinations thereof. In some embodiments, a salt, a solvate, a hydrate, a prodrug, or a metabolite of any of the foregoing compounds are administered.

Compound C10 refers to a compound having the following chemical structure:

Formula I

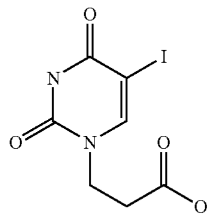

Compound C10 is available commercially from ChemDiv (San Diego, CA) as compound chemdiv4011686.

Compound C14 refers to a compound having the following chemical structure:

Formula II

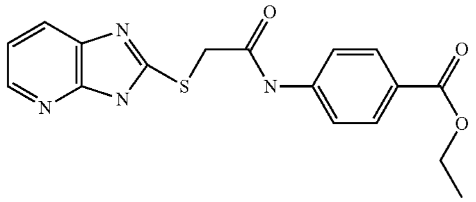

Compound C14 is available commercially from ChemDiv (San Diego, CA) as compound chemdiv4033090.

Compound C24 refers to a compound having the following chemical structure:

Formula III

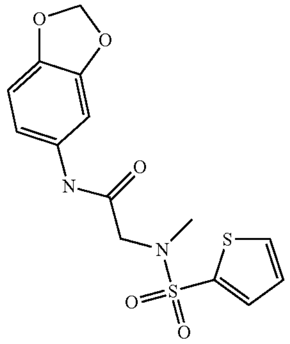

Compound C24 is available commercially from ChemDiv (San Diego, CA) as compound chemdiv4124964.

Compound C25 refers to a compound having the following chemical structure:

Formula IV

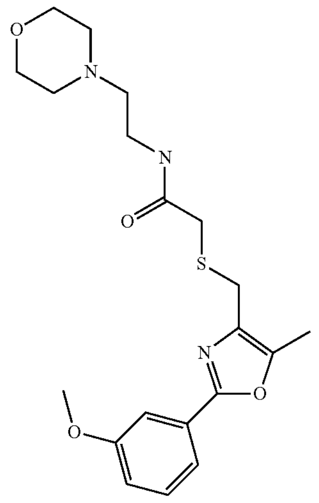

Compound C25 is available commercially from ChemDiv (San Diego, CA) as compound chemdiv4166820.

Compound C26 refers to a compound having the following chemical structure:

Formula V

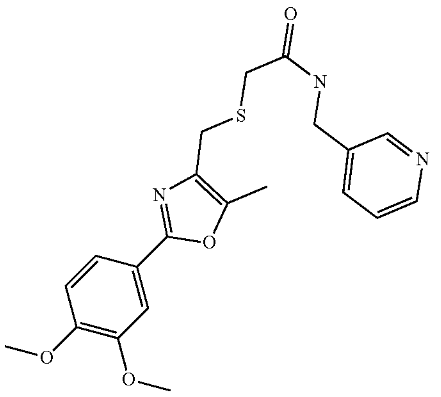

Compound C26 is available commercially from ChemDiv (San Diego, CA) as compound chemdiv4166839.

Compound C29 refers to a compound having the following chemical structure:

Formula VI

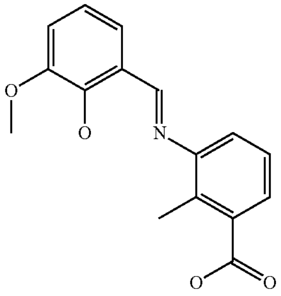

Compound C29 is available commercially from ChemDiv (San Diego, CA) as compound chemdiv193926.

Compound C29L (ortho-vanillin) refers to a compound having the following chemical structure:

Formula VII

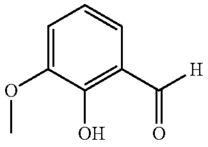

Compound C29L can be made by subjecting compound C29 to a nucleophilic cleavage step, e.g., in the presence of NaOH, to cleave the imine bond and producing C29L.

Compound C30 refers to a compound having the following chemical structure:

Formula VIII

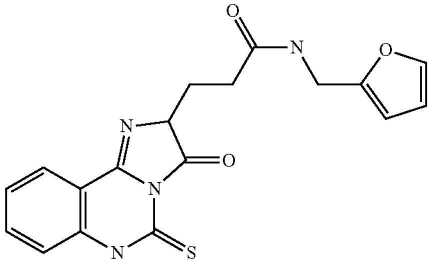

Compound C30 is available commercially from ChemDiv (San Diego, CA) as compound chemdiv4219745.

Compound C32 refers to a compound having the following chemical structure:

Formula IX

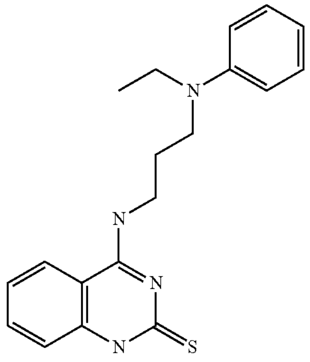

Compound C32 is available commercially from ChemDiv (San Diego, CA) as compound chemdiv0322211.

Compound C33 refers to a compound having the following chemical structure:

Formula X

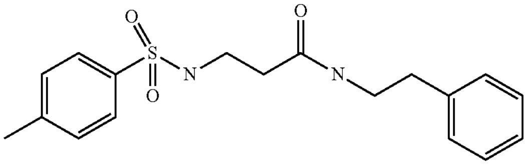

Compound C33 is available commercially from ChemDiv as compound chemdiv0328055.

In some embodiments, the invention is directed towards a method of treating a disease or condition mediated by Toll-like Receptor 2 (TLR2) in a subject, comprising administering to the subject a therapeutically effective amount of a compound selected from the group consisting of C10, C14, C24, C25, C26, C29, C29L, C30, C32, C33, and combinations thereof. In some embodiments, a salt, a solvate, a hydrate, a prodrug, or a metabolite of any of the foregoing compounds are administered.

As used herein, "treat" and all its forms and tenses (including, for example, treating, treated, and treatment) can refer to therapeutic or prophylactic treatment. In certain aspects of the invention, those in need thereof of treatment include those already with a pathological condition of the invention (including, for example, sepsis), in which case treating refers to administering to a subject (including, for example, a human or other mammal in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the patient's condition, but may not be a complete cure of the pathological condition. In other certain aspects of the invention, those in need thereof of treatment include, those in which a pathological condition is to be prevented, in which case treating refers to administering a therapeutically effective amount of a composition to a subject (including, for example, a human or other mammal in need of treatment) at risk of developing a disease or condition such as sepsis.

In accordance with the invention, a "therapeutically effective amount" or "effective amount" is administered to the subject. As used herein a "therapeutically effective amount" or "effective amount" is an amount sufficient to decrease, suppress, or ameliorate one or more symptoms associated with the disease or condition.

One skilled in the art can also readily determine an appropriate dosage regimen for administering a compound or composition of the invention to a given subject. For example, the compound(s) or composition(s) can be administered to the subject once, such as by a single injection or deposition at or near the site of interest. In some embodiments, the compound(s) or composition(s) can be administered to a subject once or twice daily to a subject once weekly for a period of from about three to about twenty-eight days, in some embodiments, from about seven to about ten weeks. In some dosage regimens, the compound(s) or composition(s) is injected at or near the site of interest once a day for seven days. Where a dosage regimen comprises multiple administrations, it is understood that the effective amount of the compound(s) or composition(s) administered to the subject can comprise the total amount of the compound(s) or composition(s) administered over the entire dosage regimen. The exact amount will depend on the purpose of the treatment, the subject to be treated, and will be ascertainable by a person skilled in the art using known methods and techniques for determining effective doses. In some embodiments, the amount of any of the compounds of Formula I-X that can be administered includes between about 0.1 μg/kg/day to about 100 mg/kg/day. In some embodiments, the amount of any of the compounds of Formula I-X that can be administered includes between about 1.0 μg/kg/day to about 10 mg/kg/day.

The inflammatory diseases of the invention are not limiting. In some embodiments, the inflammatory disease or condition involves pro-inflammatory signaling by Toll-like Receptor 2 (TLR2). Non-limiting exemplary inflammatory diseases and conditions treated by the methods of the present invention are described below.

A. Sepsis

Sepsis is a serious medical condition characterized by a whole-body inflammatory state caused by infection. Traditionally the term sepsis has been used interchangeably with septicaemia and septicemia ("blood poisoning"). However, these terms are no longer considered synonymous; septicemia is considered a subset of sepsis. Symptoms of sepsis are often related to the underlying infectious process. When the infection crosses into sepsis, the resulting symptoms are that of systemic inflammatory response syndrome (SIRS): general inflammation, fever, elevated white blood cell count (leukocytosis), and raised heart rate (tachycardia) and breathing rate (tachypnea). Secondary to the above, symptoms also include flu like chills. The immunological response that causes sepsis is a systemic inflammatory response causing widespread activation of inflammation and coagulation pathways. This may progress to dysfunction of the circulatory system and, even under optimal treatment, may result in the multiple organ dysfunction syndrome and eventually death. An underlying infection leading to sepsis can include infection by Methicillin-resistant *Staphylococcus aureus* (MRSA). Treatment of sepsis caused, at least in part, by MRSA is specifically contemplated herein.

In some embodiments, the present invention provides for treatment of sepsis, including both prophylactic treatment and treatment after sepsis has occurred.

B. Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. In some embodiments, the present invention provides for treatment of trauma, including both pre-treatment (in the case of a medical procedure) and treatment after trauma injury has occurred.

C. Acute Pancreatitis

Acute pancreatitis is rapidly-onset inflammation of the pancreas. Depending on its severity, it can have severe complications and high mortality despite treatment. While mild cases are often successfully treated with conservative measures or laparoscopy, severe cases require invasive surgery (often more than one intervention) to contain the disease process. In some embodiments, the present invention provides for treatment of acute pancreatitis, including both prophylactic treatment and treatment after acute pancreatitis has occurred.

D. Acute Respiratory Distress Syndrome

Acute respiratory distress syndrome (ARDS), also known as respiratory distress syndrome (RDS) or adult respiratory distress syndrome (in contrast with IRDS) is a serious reaction to various forms of injuries to the lung.

ARDS is a severe lung disease caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening and often lethal, usually requiring mechanical ventilation and admission to an intensive care unit. A less severe form is called acute lung injury (ALI).

ARDS can occur within 24 to 48 hours of an injury or attack of acute illness. In such a case the patient usually presents with shortness of breath, tachypnea, and symptoms related to the underlying cause, i.e., shock. Long term illnesses can also trigger it, such as malaria. The ARDS may then occur sometime after the onset of a particularly acute case of the infection.

In some embodiments, the present invention provides for treatment of ARDS and ALI, including both prophylactic treatment and treatment after ARDS or ALI has occurred.

E. Ischemia-Reperfusion Injury

Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

The damage of reperfusion injury is due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia.

Reperfusion injury plays a part in the brain's ischemic cascade, which is involved in stroke and brain trauma. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

In some embodiments, the present invention provides for treatment of ischemia-reperfusion injury, including both prophylactic treatment and treatment after ischemia-reperfusion injury has occurred.

F. Cardiovascular Disease

Cardiovascular disease refers to the class of diseases that involve the heart or blood vessels (arteries and veins). While the term technically refers to any disease that affects the cardiovascular system, it is usually used to refer to those related to atherosclerosis (arterial disease). These conditions have similar causes, mechanisms, and treatments. Treatment of cardiovascular disease depends on the specific form of the disease in each patient, but effective treatment always includes preventive lifestyle changes discussed above. Medications, such as blood pressure reducing medications, aspirin and the statin cholesterol-lowering drugs may be helpful. In some circumstances, surgery or angioplasty may be warranted to reopen, repair, or replace damaged blood vessels.

Atherosclerosis (also known as arteriosclerotic vascular disease or ASVD) is a specific form of arteriosclerosis in which an artery-wall thickens as a result of invasion and accumulation of white blood cells (WBCs) (foam cell) and proliferation of intimal-smooth-muscle cell creating a fibro-fatty plaque.

In some embodiments, the present invention provides for treatment of cardiovascular disease, including both prophylactic treatment and treatment after cardiovascular disease has occurred.

G. Autoimmune/Inflammatory Disease

In some embodiments, the present invention provides for treatment of a variety of autoimmune and/or inflammatory disease states such as spondyloarthropathy, ankylosing spondylitis, psoriatic arthritis, reactive arthritis, enteropathic arthritis, ulcerative colitis, Crohn's disease, irritable bowel disease, inflammatory bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, or psoriasis. The diagnosis and treatment of these diseases are well documented in the literature.

H. Chemotherapy, Radiotherapy and Cytokine Therapy Toxicity

Various forms of cancer therapy, including chemotherapy, radiation, and cytokines, are associated with toxicity, sometimes severe, in the cancer patient. To the extent that the toxicity is caused at least in part by the extracellular actions of histones, in some embodiments, the present invention seeks to reduce this toxicity using the pharmaceutical compositions of the present invention, thereby reducing or alleviating discomfort on the part of the patient, as well as permitting higher doses of the therapy.

I. Burns

A burn may be an injury caused by heat, cold, electricity, chemicals, friction or radiation. First-degree burns are usually limited to redness (erythema), a white plaque, and minor pain at the site of injury. These burns usually extend only into the epidermis. Second-degree burns additionally fill with clear fluid, have superficial blistering of the skin, and can involve more or less pain depending on the level of nerve involvement. Second-degree burns involve the superficial (papillary) dermis and may also involve the deep (reticular) dermis layer. Third-degree burns additionally have charring of the skin, and produce hard, leather-like eschars. Serious burns, especially if they cover large areas of the body, can cause death; any hint of burn injury to the lungs (e.g., through smoke inhalation) is a medical emergency.

Burns that injure the tissues underlying the skin, such as the muscles or bones, are sometimes categorized as fourth-degree burns. These burns are broken down into three additional degrees: fourth-degree burns result in the skin being irretrievably lost, fifth-degree burns result in muscle being irretrievably lost, and sixth-degree burns result in bone being charred.

In some embodiments, the present invention provides for treatment of burns, including both prophylactic treatment and treatment after cardiovascular disease has occurred.

J. Tumor Metastasis

Although cancer cells grow infinitely at specific sites, they can also leave the sites from which they originated, migrate to and grow in new sites, whose process is called "metastasis". Cancer at the new site is a "tumor metastasis." Metastasis involve several key steps: conversion of cancer cells to migratory mesenchymal cells, dissociation of the mesenchymal cells from the original tumor sites, invasion into and spread through surrounding connective tissues and capillary vessels, migration through blood vessels, escape from the blood vessels, migration through connective tissues, and proliferation in secondary sites. The complex and highly selective metastatic cascade depends on the intrinsic properties of tumor cells and the microenvironment that they derive from. An inflammatory milieu consisting of infiltrated immune cells and their secretory cytokines, chemokines and growth factors contribute significantly to the invasive and metastatic traits of cancer cells.

In some embodiments, the present invention provides for treatment of metastasis.

In some embodiments, the inflammatory disease or condition is selected from the group consisting of sepsis, trauma, acute pancreatitis, acute respiratory distress syndrome, ischemia-reperfusion injury, cardiovascular disease, autoimmune disease, toxicity caused by chemotherapy, radiotherapy and cytokine therapy, burns, and tumor metastasis.

The term "subject" as used herein is not limiting and is used interchangeably with patient. In some embodiments, the subject is a mammal. For example, mammals contemplated include humans, primates, dogs, cats, sheep, cattle, goats, pigs, horses, chickens, mice, rats, rabbits, guinea pigs, and the like. In some embodiments, the subject is a human.

In some embodiments, administration of the compound of the invention inhibits signaling by Toll-like Receptor 2 (TLR2). In some embodiments, the compound inhibits signaling by TLR2 by about 5%, 10%, 15%, 20%, 25%, 30%, 35%, 40%, 45%, 50%, 55%, 60%, 65%, 70%, 75%, 80%, 85%, 90%, 95% or 100%.

In some embodiments, the compound inhibits signaling by TLR2 by inhibiting interactions between TLR2 and Myeloid Differentiation Primary Response 88 (MyD88) protein. In some embodiments, the compound inhibits signaling by TLR2 by inhibiting MyD88 interactions with TLR2/TLR1 and/or TLR2/TLR6. In some embodiments, the compound inhibits signaling by TLR2 by inhibiting MyD88 interactions with TLR2/TLR1 but not TLR2/TLR6. In some embodiments, the compound inhibits signaling by TLR2 by inhibiting MyD88 interactions with TLR2/TLR6 but not TLR2/TLR1. In some embodiments, the compound inhibits signaling by TLR2 by inhibiting MyD88 interactions with TLR2/TLR1 to a greater degree than MyD88 interactions with TLR2/TLR6. In some embodiments, the compound inhibits signaling by TLR2 by inhibiting MyD88 interactions with TLR2/TLR6 to a greater degree than MyD88 interactions with TLR2/TLR1. In some embodiments, the compound inhibits signaling by TLR2 by inhibiting MyD88 interactions with TLR2/TLR6 and TLR2/TLR1 to the same degree.

In some embodiments, the compound inhibits interactions between TLR2 and MyD88 by about 5%, 10%, 15%, 20%, 25%, 30%, 35%, 40%, 45%, 50%, 55%, 60%, 65%, 70%, 75%, 80%, 85%, 90%, 95% or 100%.

In some embodiments, the compound inhibits MyD88 interactions with TLR2/TLR1 and/or TLR2/TLR6 by about 5%, 10%, 15%, 20%, 25%, 30%, 35%, 40%, 45%, 50%, 55%, 60%, 65%, 70%, 75%, 80%, 85%, 90%, 95% or 100%.

In some embodiments, administration of the compound inhibits signaling by TLR2/TLR1 and/or TLR2/TLR6.

In some embodiments, the compound inhibits signaling by TLR2 by inhibiting binding of TLR2 with TLR6 or TLR1. In some embodiments, the compound inhibits signaling by TLR2 by inhibiting ligand binding to TLR2/TLR1 and/or TLR2/TLR6.

In some embodiments, the compound inhibits binding of TLR1 to TLR2, but not binding of TLR2 to TLR6. In some embodiments, the compound inhibits binding of TLR1 to TLR6, but not binding of TLR2 to TLR1. In some embodiments, the compound inhibits ligand binding to TLR1/TLR2, but not to TLR2/TLR6. In some embodiments, the compound inhibits ligand binding to TLR1/TLR6, but not to TLR2/TLR1.

In some embodiments, the compound inhibits binding of TLR2 to TLR1 and/or TLR6 by about 5%, 10%, 15%, 20%, 25%, 30%, 35%, 40%, 45%, 50%, 55%, 60%, 65%, 70%, 75%, 80%, 85%, 90%, 95% or 100%.

In some embodiments, the compound inhibits ligand binding to TLR2/TLR1 and/or TLR2/TLR6 by about 5%, 10%, 15%, 20%, 25%, 30%, 35%, 40%, 45%, 50%, 55%, 60%, 65%, 70%, 75%, 80%, 85%, 90%, 95% or 100%. In some embodiments, the compound inhibits binding of TLR2 to both TLR1 and TLR 6 equally. In some embodiments, the compound inhibits binding of TLR2 to TLR1 to a greater degree than binding of TLR2 to TLR6. In some embodiments, the compound inhibits binding of TLR2 to TLR1 to a lesser degree than binding of TLR2 to TLR6.

In some embodiments, administration of the compound does not inhibit TNF-α-induced signaling. In some embodiments, administration of the compound inhibits TNF-α-induced signaling. In some embodiments, administration of the compound inhibits TLR2 signaling to a greater degree than TNF-α-induced signaling.

In some embodiments, the compound is C29 or C29L. In some embodiments, the compound is administered in a composition comprising a pharmaceutically acceptable excipient.

The compound(s) or composition(s) of the disclosure may be formulated as pharmaceutical compositions prior to administration to a subject, according to techniques known in the art. See, e.g., Remington's Pharmaceutical Science, 17th ed., Mack Publishing Company, Easton, Pa. (1985), the entire disclosure of which is herein incorporated by reference. In some embodiments, pharmaceutical compositions of the present invention are characterized as being at least sterile and pyrogen-free. As used herein, "pharmaceutical formulations" include formulations for human and veterinary use.

Suitable routes of administration may, for example, include oral, rectal, transmucosal, buccal, intravaginal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the compound in a targeted drug delivery system, for example in a liposome. Suitable parenteral delivery include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intra-retinal injection or subretinal injection); subcutaneous injection or deposition including subcutaneous infusion (such as by osmotic pumps); direct (e.g., topical) application to the area at or near the site of interest, for example by a catheter or other placement device (e.g., a corneal pellet or a suppository, eye-dropper, or an implant comprising a porous, non-porous, or gelatinous material); and inhalation. In a particular embodiment, injections or infusions of the composition(s) are given at or near the site of disease or condition.

In some embodiments, the compound or composition is administered by injection. In some embodiments, the compound or composition can be administered by intramuscular or intravenous injection.

In one embodiment, the invention is directed towards an anti-inflammatory composition comprising an effective amount of the compound selected from the group consisting of C10, C14, C24, C25, C26, C29, C29L, C30, C32, and C33, or salt, solvate, hydrate, prodrug, metabolite, or combination thereof, and a pharmaceutically acceptable excipient. In some embodiments, the composition comprises C29 or C29L, or salt, solvate, hydrate, prodrug, metabolite, or combination thereof. In some embodiments, the invention is directed towards a pharmaceutical composition comprising compound C29L or salt, solvate, hydrate, prodrug, or metabolite thereof. In some embodiments, the compound C29L is part of a pharmaceutical composition as described herein.

In some embodiments, compositions of the disclosure can comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). In some embodiments, pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like. For example, a solid pharmaceutical composition for oral administration can comprise any of the carriers and excipients listed above and 10-95%, or 25%-75%, of one or more compound(s) or compositions of the invention. In some embodiments, a pharmaceutical composition for aerosol (inhalational) administration can comprise 0.01-20% by weight or 1%-10% by weight, of one or more compound(s) or compositions of the invention encapsulated in a liposome as described herein, and propellant. A carrier can also be included as desired; e.g., lecithin for intranasal delivery.

In one embodiment, the invention is directed towards a method for making C29L, comprising subjecting compound C29 to a nucleophilic cleavage step to cleave the imine bond and producing C29L. Any suitable nucleophile may be used to cleave the imine bond and is not limiting. In some embodiments, the nucleophilic cleavage step involves contacting C29 with NaOH. In some embodiments, the nucleophilic cleavage step involves reacting C29 in solution with about 65 μM NaOH.

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

EXAMPLES

Example 1

Screening of Potential TLR2 Inhibitors

Figure 5:
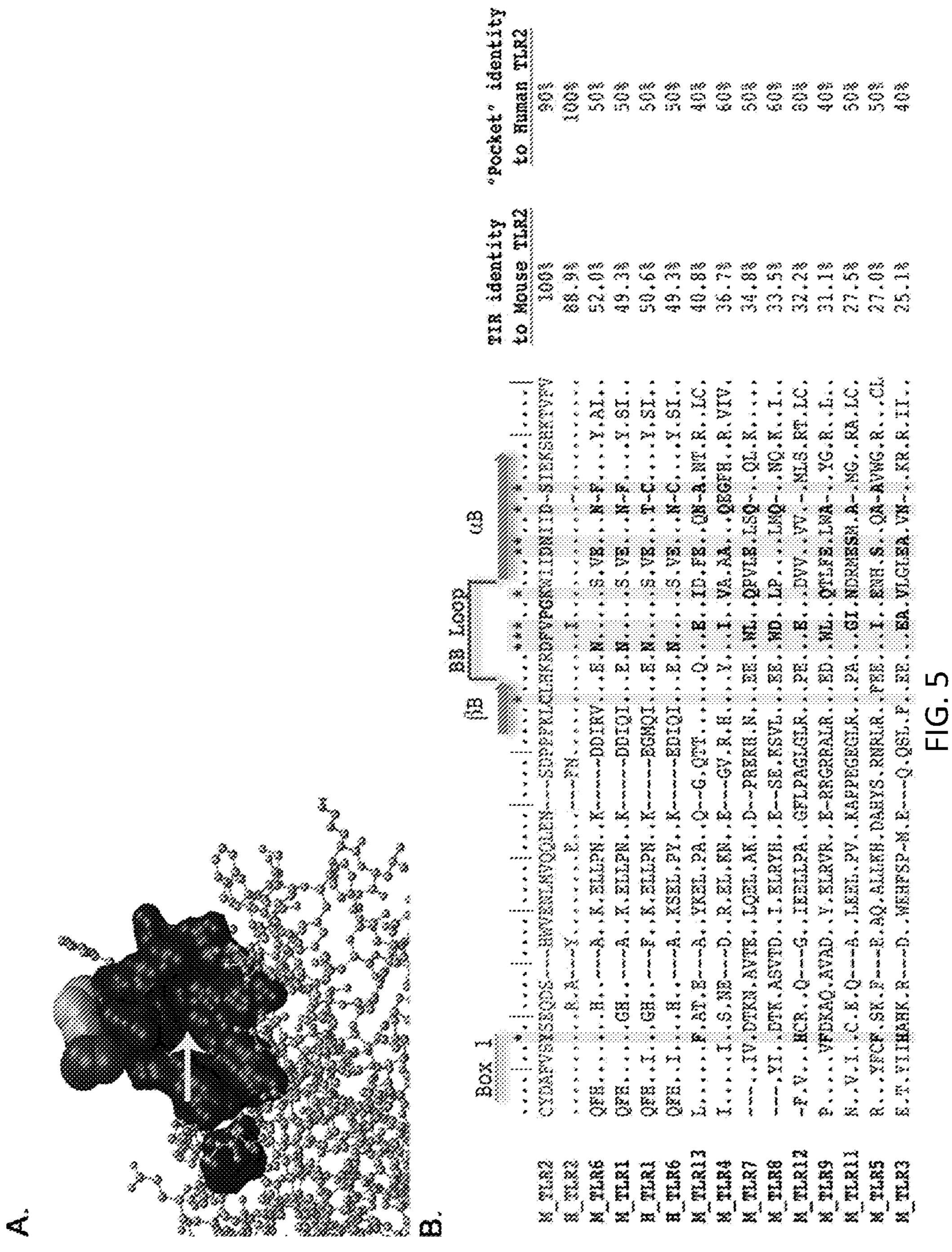
FIG. 5. TLR2 TIR structure and alignment. (A) Molecular model of the TLR2 TIR domain (PDB ID: 1FYW) (silver) with arrow indicating the CADD-targeted BB loop pocket (blue). Conserved P681 (red) and G682 (green) residues of the BB loop are found adjacent to the CADD-targeted pocket. Visual Molecular Dynamics program was used to generate this molecular model (70). (B) Comparison of TIR domains from mouse (M) and human (H) TLRs based on amino acid alignment. Residues identical to the mouse TLR2 sequence are indicated with a dot. Yellow-highlight and bold type beneath asterisks (*) indicates residues that form the CADD-targeted pocket. Bold type in blue identifies the conserved P681-G682 residues of the BB loop. Percent protein identity across the entire TIR domain as well as the CADD-targeted pocket are given.

Visual inspection of the crystal structure of the TLR2 TIR domain (PDB ID: 1FYW) revealed the BB loop pocket (Y647, C673, D678, F679, I680, K683, D687, N688, D691, and S692) adjacent to the conserved P681 and G682 residues of the BB loop (FIG. 5). Over one million commercially available small compounds, as well as FDA-approved drugs, were screened in silico for those that could potentially fit into the pocket. CADD analysis identified ~1000 compounds based on predicted favorable interactions with the TLR2 BB loop pocket. Of these, 149 chemically diverse small molecules and 20 FDA-approved drugs with physiochemical properties that should maximize bioavailability and ranked highest for their potential to fit into the TLR2 TIR pocket were screened for their ability to inhibit TLR2-mediated signaling.

Figure 6:
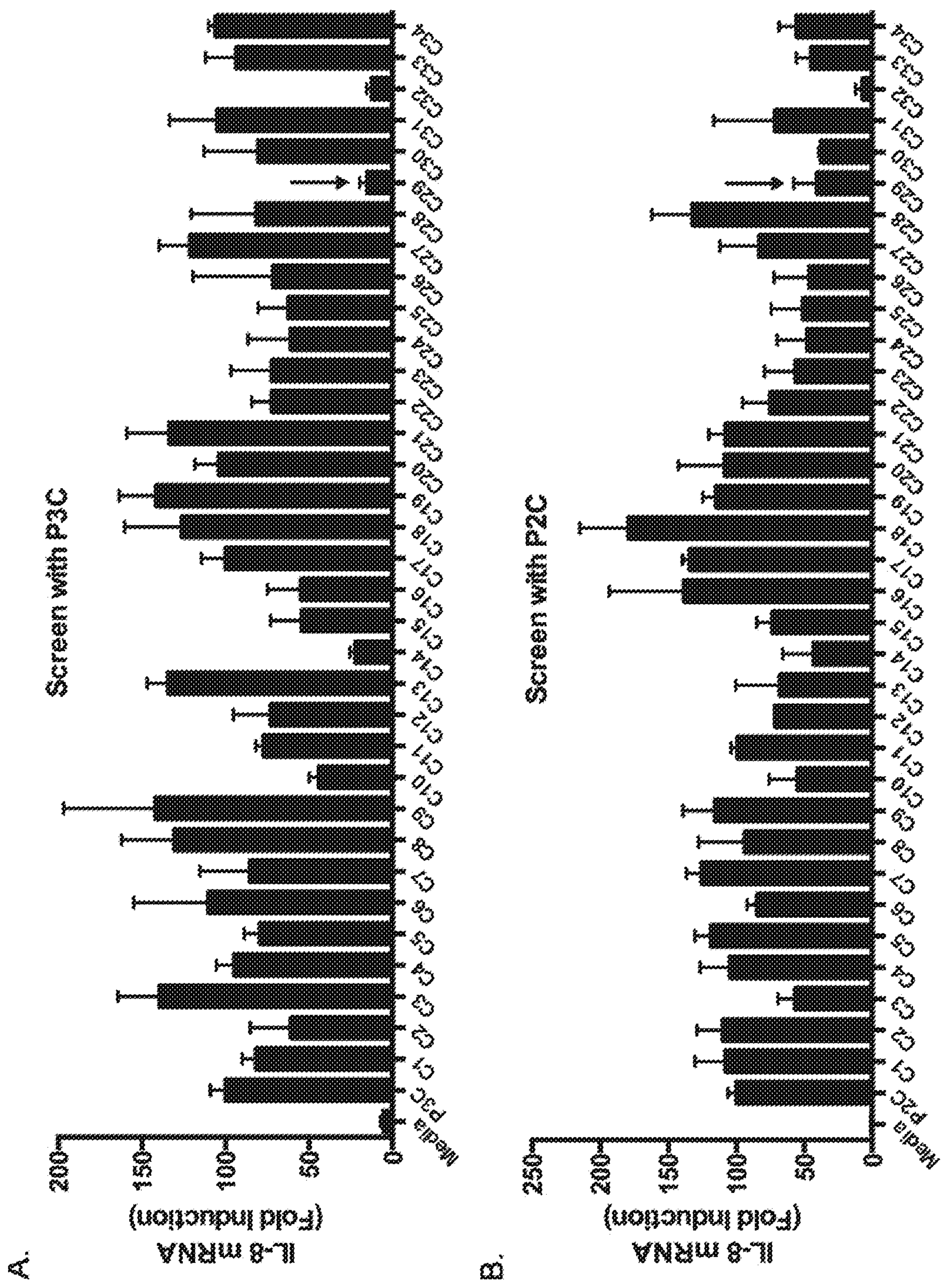
FIG. 6. Initial in vitro screening of potential TLR2 inhibitors. (A, B) Total RNA was extracted from HEK-TLR2 cells pretreated for 1 hr with 100 μM of the indicated compound and then stimulated with P3C (100 ng/mL) (A) or P2C (5 ng/mL) (B) for 1 hr in the presence of the compound. IL-8 mRNA was measured as described in FIG. 1, panel B. Arrow indicates C29. Quantitative real-time results shown are the mean±SEM from at least 3 independent experiments each carried out in duplicate.

Initially, 34 compounds (C1-C34) were tested in stably transfected HEK-hTLR2 cells for the ability to block N-Palmitoyl-S-[2,3-bis(palmitoyloxy)-(2RS)-propyl]-(R)-cysteinyl-(S)-seryl-(S)-lysyl-(S)-lysyl-(S)-lysyl-(S)-lysine (P3C)— and S-[2,3-bis(palmitoyloxy)-(2RS)-propyl]-(R)-cysteinyl-(S)-seryl-(S)-lysyl-(S)-lysyl-(S)-lysyl-(S)-lysine (P2C)-induced IL-8 mRNA via TLR2/1 and TLR2/6 signaling pathways, respectively. Four compounds, i.e., C10, C14, C29, and C32, consistently decreased P3C-induced IL-8 mRNA by ≥50% (FIG. 6, panel A) and 8 compounds, i.e., C14, C29, and C32, as seen in P3C-induced signaling, as well as C24, C25, C26, C30, and C33, decreased P2C-induced IL-8 mRNA by ≥50% (FIG. 6, panel B). These results provided indicate that CADD is an effective first step for the identification of potential small molecule inhibitors of TLR2 signaling.

C29 Blunts Human TLR2/1 and TLR2/6 Signaling in HEK-TLR2 Stable Transfectants and THP-1 Cells.

Figure 7:
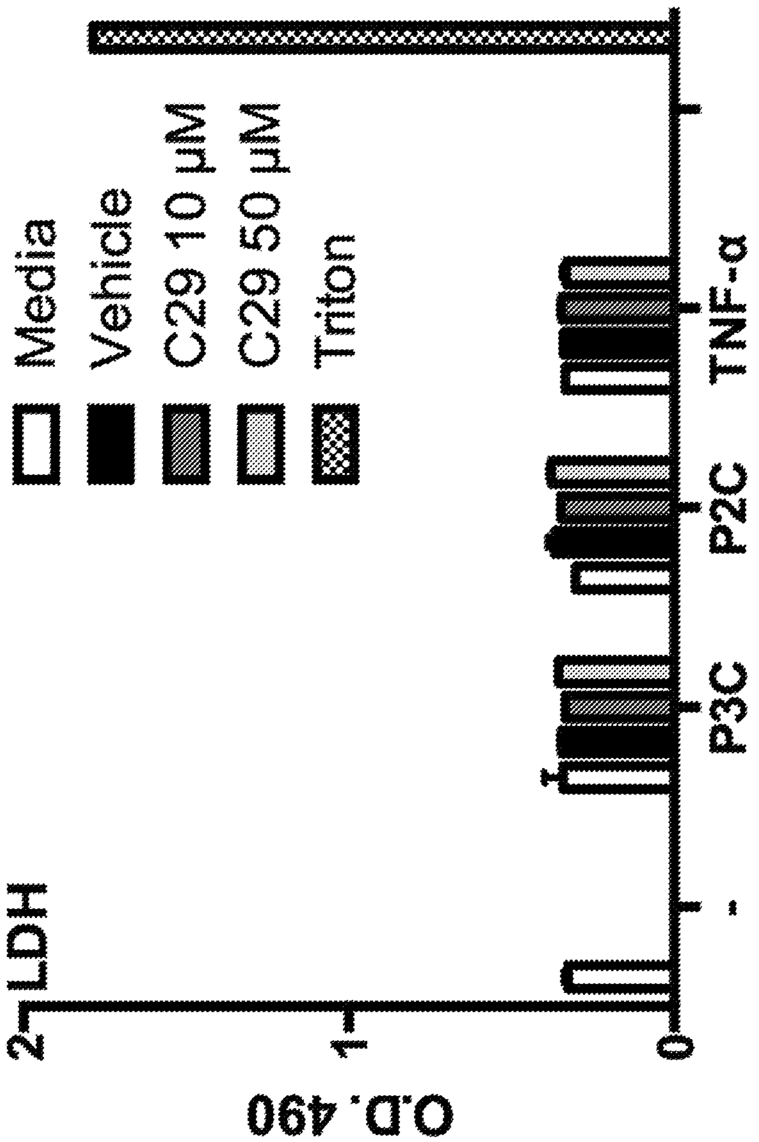
FIG. 7. C29 is not cytotoxic to HEK-TLR2 stable transfectants. Cells were pretreated for 1 hr with media, vehicle (65 μM NaOH), or C29 (10 μM or 50 μM) and then stimulated with P3C (200 ng/mL), P2C (200 ng/mL), or hTNF-α (300 ng/mL) for 1 hr in the presence of media, vehicle, or C29. Supernatants of cell cultures were collected and analyzed for LDH release as a measure of cell cytotoxicity with Triton X-lysed cells serving as the positive control. LDH release is representative of 1 of 2 independent experiments carried out in duplicate.

These potential TLR2 inhibitors were tested to assess dose-dependency and cytotoxicity. Compound C29 ($C_{16}H_{15}NO_4$; FIG. 1, panel A) blocked P3C- and P2C-induced IL-8 mRNA dose-dependently in HEK-TLR2 stable transfectants, while having no effect on TNF-α-induced signaling or on cytotoxicity (FIG. 1, panel B and FIG. 7).

Figure 8:
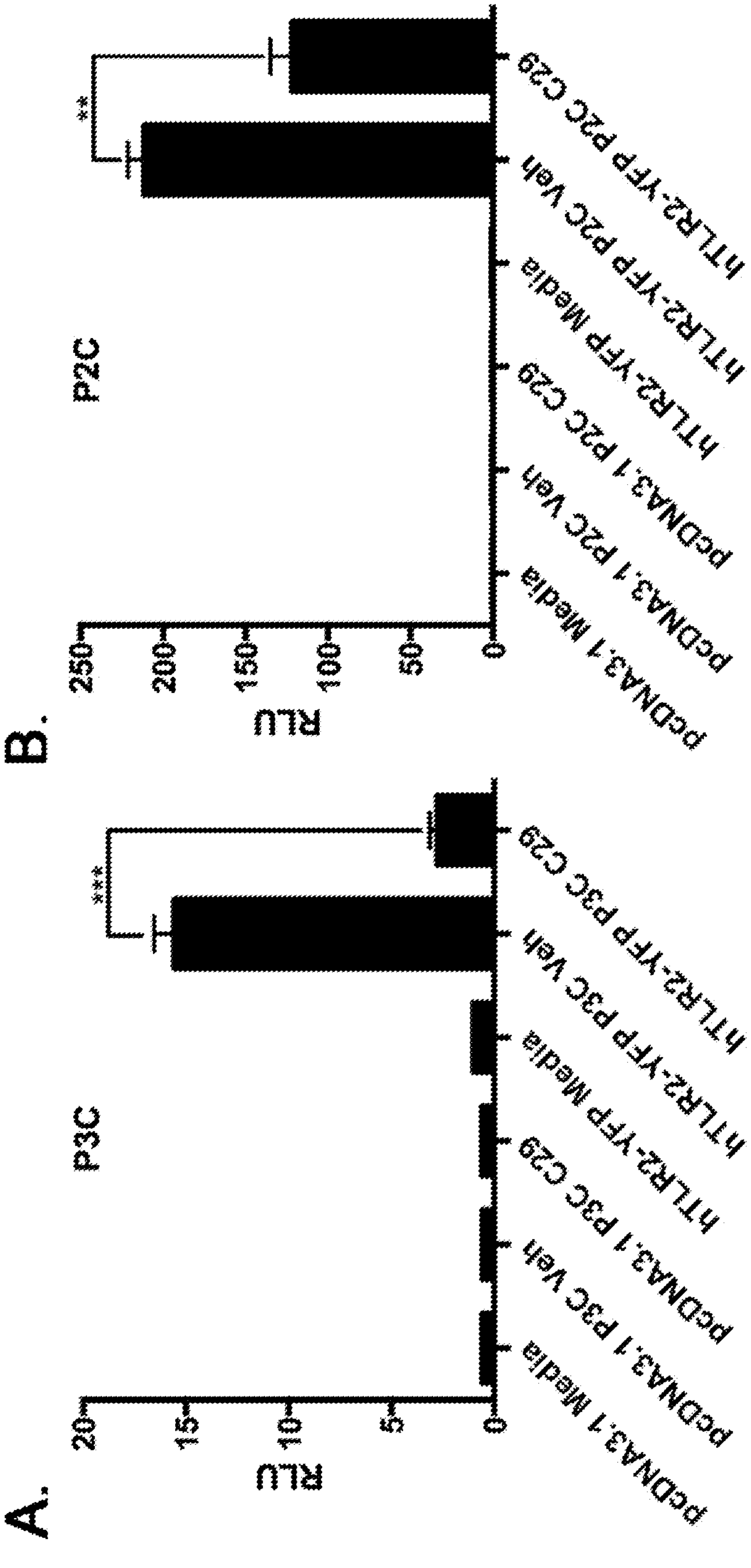
FIG. 8. C29 inhibits hTLR2/1- and hTLR2/6-induced NF-κβ activation. (A, B) HEK293T cells were transiently transfected with reporter constructs for ELAM-luciferase, *Renilla*-luciferase, and either pcDNA3.1 or pcDNA3-YFP-hTLR2. Cells were pretreated for 1 hr with media, vehicle (65 μM NaOH), or C29 (50 μM) and treated with P3C or P2C (50 ng/mL) for 5 hrs in the presence of media, vehicle, or C29. Lysates were prepared and the dual-luciferase assay performed. Results are representative of 3 independent experiments each carried out in duplicate (, p≤0.01; *, p≤0.001).
Figure 9:
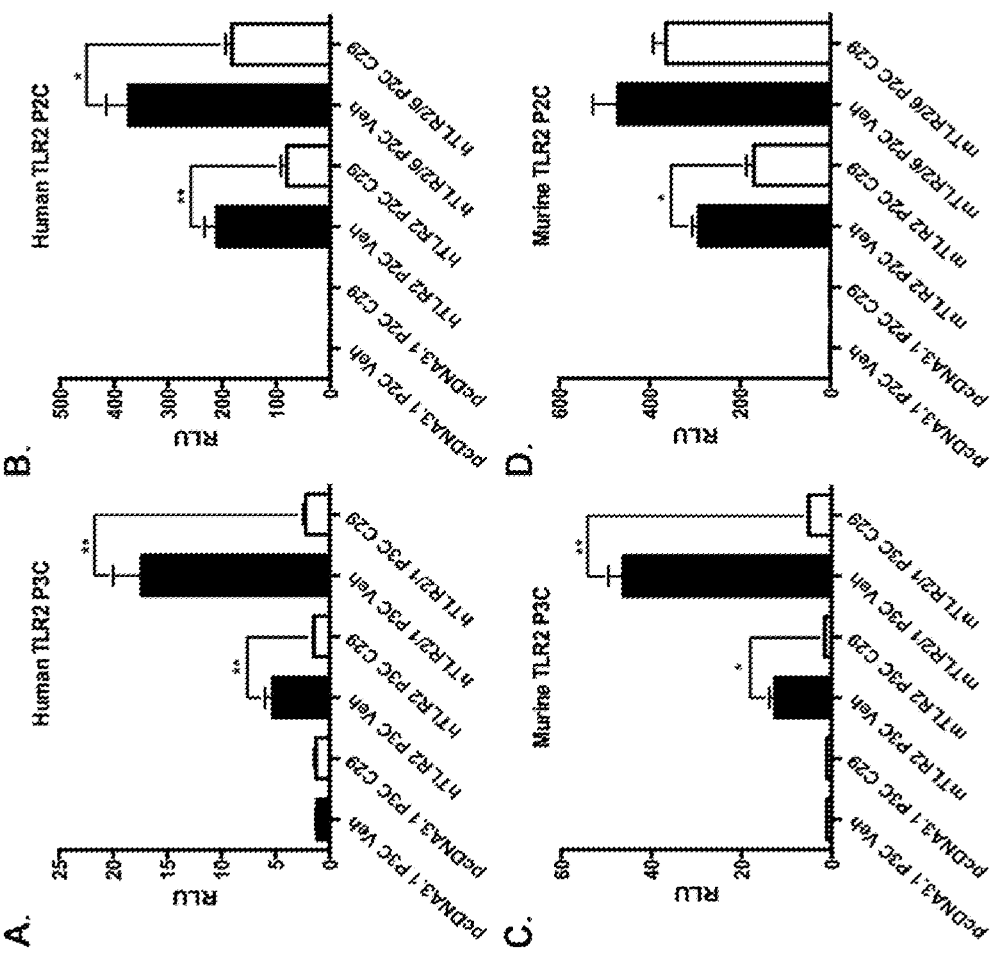
FIG. 9. C29 is species-specific and blocks human TLR2/6 signaling, but not murine TLR2/6 signaling. (A-D) HEK293T cells were transiently transfected with reporter constructs for ELAM-luciferase, *Renilla*-luciferase, and pcDNA3.1 in combination with/without pcDNA3-YFP-hTLR2, pFLAG-CMV1-hTLR1, pcDNA3-CFP-hTLR6, pcDNA3.1-mTLR2-CFP, pcDNA3.1-mTLR1-YFP, or pcDNA3.1-mTLR6-CFP. Cells were pretreated for 1 hr with media, vehicle (65 μM NaOH), or C29 (50 μM) and then treated with P3C or P2C (50 ng/mL) for 5 hrs in the presence of media, vehicle, or C29. Lysates were prepared and the dual-luciferase assay performed. Panels A and B represent the mean±SEM from 3 independent experiments and panels C and D represent the mean±SEM from 2 independent experiments each carried out in duplicate (*, p≤0.05; **, p≤0.01).

The effect of C29 on TLR2 signaling in the human THP-1 macrophage-like cell line (28): C29 also inhibited P3C- and P2C-induced IL-1β gene expression significantly at both 1 h and 4 h following stimulation (FIG. 1, panel C), as well as both P3C- and P2C-induced NF-κβ-luciferase activity in transiently transfected HEK293T cells expressing human TLR2 and an NF-κβ-sensitive luciferase reporter construct (FIG. 8). Thus, C29 inhibits both TLR2/1 and TLR2/6 signaling in human cell lines.

C29 Preferentially Inhibits TLR2/1 Signaling in Primary Murine Macrophages.

Based on the high degree of amino acid sequence identity between human and murine TLR2 TIR domains (88.9%) and within the BB loop pocket (90%) (FIG. 5, panel B), it was hypothesized that C29 would also block TLR2 signaling in murine macrophages. Interestingly, C29 significantly reduced P3C-, but not P2C-induced TNF-α mRNA and IL-12 p40 protein (FIG. 1, panels D-F), in contrast to the human cells where C29 inhibited both TLR2/1 and TLR2/6 signaling pathways (FIG. 1, panels B and C and FIG. 8). To determine whether this was a species-specific or a cell-specific effect, HEK293T cells were transfected with plasmids encoding either human or murine TLR2 and either TLR1 or TLR6 and the effect of C29 on TLR2/1 and TLR2/6 signaling was assessed using our NF-κβ reporter assay. C29 significantly inhibited hTLR2/6-, but not mTLR2/6-induced NF-κβ-luciferase activity (FIG. S5). The data herein suggest that the difference of C29 to block human TLR2/6 signaling and not murine TLR2/6 signaling is species-specific.

Figure 10:
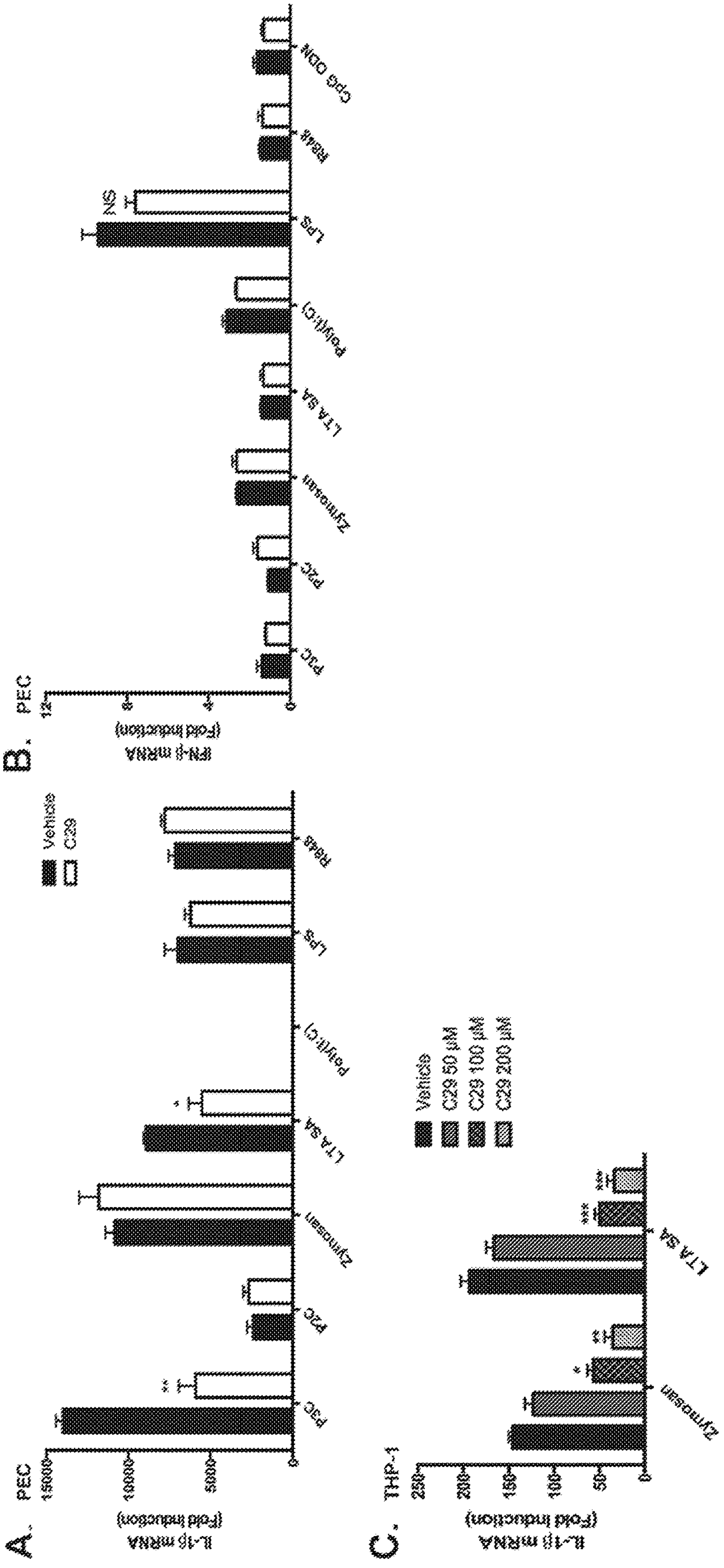
FIG. 10. Examining the broader specificity of C29 for TLR2 signaling. (A, B) Total RNA was extracted from murine macrophages that had been pretreated for 1 hr with vehicle (65 μM NaOH) or C29 (50 μM) and then stimulated with P3C (50 ng/mL), P2C (100 ng/mL), zymosan (10 μg/mL), *S. aureus* LTA (1 μg/mL), poly(I:C) (10 μg/mL), LPS (100 ng/mL), R848 (10 μg/mL), or CpG ODN 1668 (5 μM) for 3 hrs in the presence of vehicle or C29. IL-1β and IFN-β mRNA were measured as described in FIG. 1, panel D. (C) THP-1 cells were plated in the presence of PMA (20 ng/mL) for 24 hrs and washed twice in media. Total RNA was extracted from cell cultures pretreated for 1 hr with vehicle (260 μM NaOH) or C29 (50 μM, 100 μM, or 200 μM) and then stimulated with zymosan (10 μg/mL) or *S. aureus* LTA (1 μg/mL) for 4 hrs in the presence of vehicle or C29. IL-1β mRNA was measured as described in FIG. 1, panel B. Quantitative real-time results represent the mean±SEM from 2 independent experiments each carried out in duplicate (*, p≤0.05; , p≤0.01; *, p≤0.001).

The specificity of C29 for TLR2/1 in murine cells was further assessed by testing additional TLR2 agonists including *S. aureus* lipoteichoic acid (LTA SA), a TLR2/1 agonist (Schroder N W, et al. (2003) *The Journal of biological chemistry* 278(18):15587-15594), and zymosan, shown previously to activate TLR2/6 (Ozinsky A, et al. (2000) *Proceedings of the National Academy of Sciences of the United States of America* 97(25):13766-13771), as well as other TLR agonists. C29 specifically blocked P3C- and LTA SA-induced IL-1β mRNA in murine macrophages (FIG. 10, panel A). Like P2C (FIG. 1, panel E), C29 did not inhibit zymosan-induced IL-1β mRNA in murine macrophages (FIG. 10, panel A). Moreover, C29 had no significant inhibitory effect on the MyD88-independent pathway in murine macrophages when stimulated with agonists that induce IFN-β (FIG. 10, panel B). C29 blocked zymosan- and LTA SA-induced IL-1β mRNA dose-dependently in human THP-1 cells (FIG. 10, panel C). In summary, C29 blocks only TLR2/1-mediated cytokine mRNA and protein in primary murine macrophages.

C29 Blocks TLR2 Bacterial Agonist-Induced Proinflammatory Gene Expression in HEK-TLR2 Cells and Murine Macrophages.

TLR2 dimerization with TLR1 or TLR6 allows for recognition of both Gram-positive and certain Gram-negative bacteria, e.g., *S. aureus, S. pneumoniae, Ps. aeruginosa*, and *F. tularensis* (Cole L E, et al. (2006) *Journal of immunology* 176(11):6888-6899; Medina E A, Morris I R, & Berton M T (2010) *Journal of immunology* 185(12):7562-7572; Raoust E, et al. (2009) *PloS one* 4(10):e7259; Yoshimura A, et al. (1999) *Journal of immunology* 163(1):1-5). C29 significantly inhibited heat-killed *Ps. aeruginosa* (HKPA)- and *S. aureus* (HKSA)-induced IL-8 mRNA in HEK-TLR2 cells (FIG. 1, panel G). C29 also significantly inhibited IL-8 mRNA in HEK-TLR2 cells stimulated by live *F. tularensis* (FIG. 1, panel H), a TLR2/6 agonist (Cole L E, et al. (2006) *Journal of immunology* 176(11):6888-6899; Cole L E, et al. (2007) *Infection and immunity* 75(8):4127-4137; Katz J, et al. (2006) *Infection and immunity* 74(5):2809-2816). In primary murine macrophages (PEC), C29 significantly blocked heat-killed *S. pneumoniae* (HKSP)- and HKSA-mediated IL-1β mRNA (FIG. 1, panel I). In contrast, IL-1β mRNA induced by heat-killed *Escherichia coli* (HKEC), which signals predominately through TLR4, was not blocked by C29, in contrast to P3C-induced IL-1β mRNA (FIG. 1, panel J). C29 also inhibited IL-1β and IL-12 p40 mRNA in murine macrophages stimulated with live *S. pneumoniae* (FIG. 1, panels K and L). Thus, C29 blocks cytokine gene expression induced by heat-killed or live bacterial TLR2 agonists in human HEK-TLR2 transfectants and in murine macrophages.

C29 Inhibits Ligand-Induced Interaction of TLR2 with MyD88 and Blocks MAPK and NF-κβ Activation.

Figure 2:
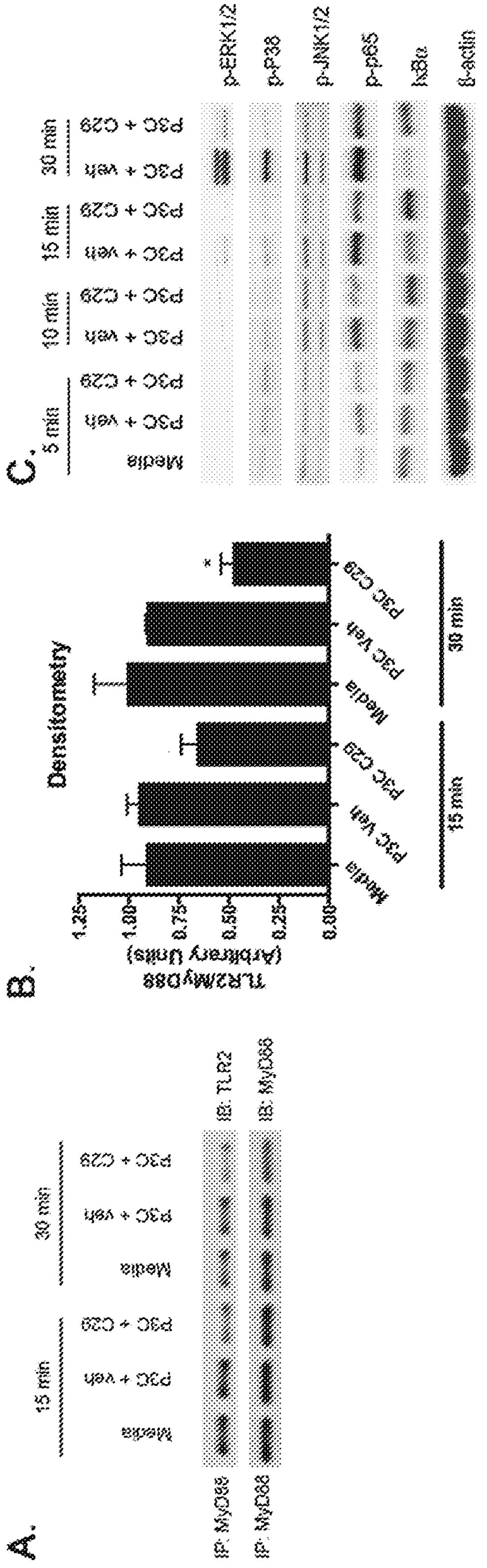
FIG. 2. C29 inhibits ligand-induced interaction of TLR2 with MyD88 and blocks MAPK and NF-κβ activation. (A) THP-1 cells were cultured in the presence of PMA (20 ng/mL) for 24 hrs and washed twice in media. THP-1 human monocytes were pretreated with media, vehicle (195 μM NaOH), or C29 (150 μM) for 1 hr and treated with P3C (50 ng/mL) in the presence of media, vehicle, or C29 for 15 or 30 min. Co-immunoprecipitation (IP) was carried out using anti-MyD88 antibody and Western analysis (IB) using whole cell lysates. (B) Densitometry analysis (mean±SEM) of 3 independent experiments as shown in (A). (C) Murine peritoneal macrophages were pretreated for 1 hr with media, vehicle (65 μM NaOH), or C29 (50 μM) and treated with P3C (50 ng/mL) for 5-30 min in the presence of media, vehicle, or C29. IB was performed using whole cell lysates and antibodies directed against the signaling intermediates indicated. β-actin was probed as a loading protein. Panel A is representative of 3 independent experiments and panel B is the mean±SEM from 3 independent experiments (*, $p \leq 0.05$). Panel B is representative of 2 independent experiments.

Previous studies demonstrated that the P681H mutation within the BB loop of human TLR2 abolishes MyD88 recruitment and thereby blunts signaling (Brown V, et al. (2006) *European journal of immunology* 36(3):742-753; Xu Y, et al. (2000) *Nature* 408(6808):111-115). In THP-1 cells, C29 treatment diminished the interaction between endogenous TLR2 and MyD88 at 15 and 30 minutes post-stimulation with P3C compared to vehicle control and achieved statistical significance at 30 minutes. Densitometry analysis of 3 independent experiments confirmed this finding (FIG. 2, panels A and B).

TLR2 recruitment of MyD88 activates NF-κβ and MAPKs. Upon P3C stimulation, C29 blocked robust MAPK activation at 30 min and reduced NF-κβ activation from 5 to 30 min (FIG. 2, panel C). C29 prevented P3C-induced degradation of IκBα at 15 and 30 min (FIG. 2, panel C).

TLR2 BB Loop Pocket Mutants Reveal Divergent Roles in TLR2/1 and TLR2/6 Signaling.

Figure 3:
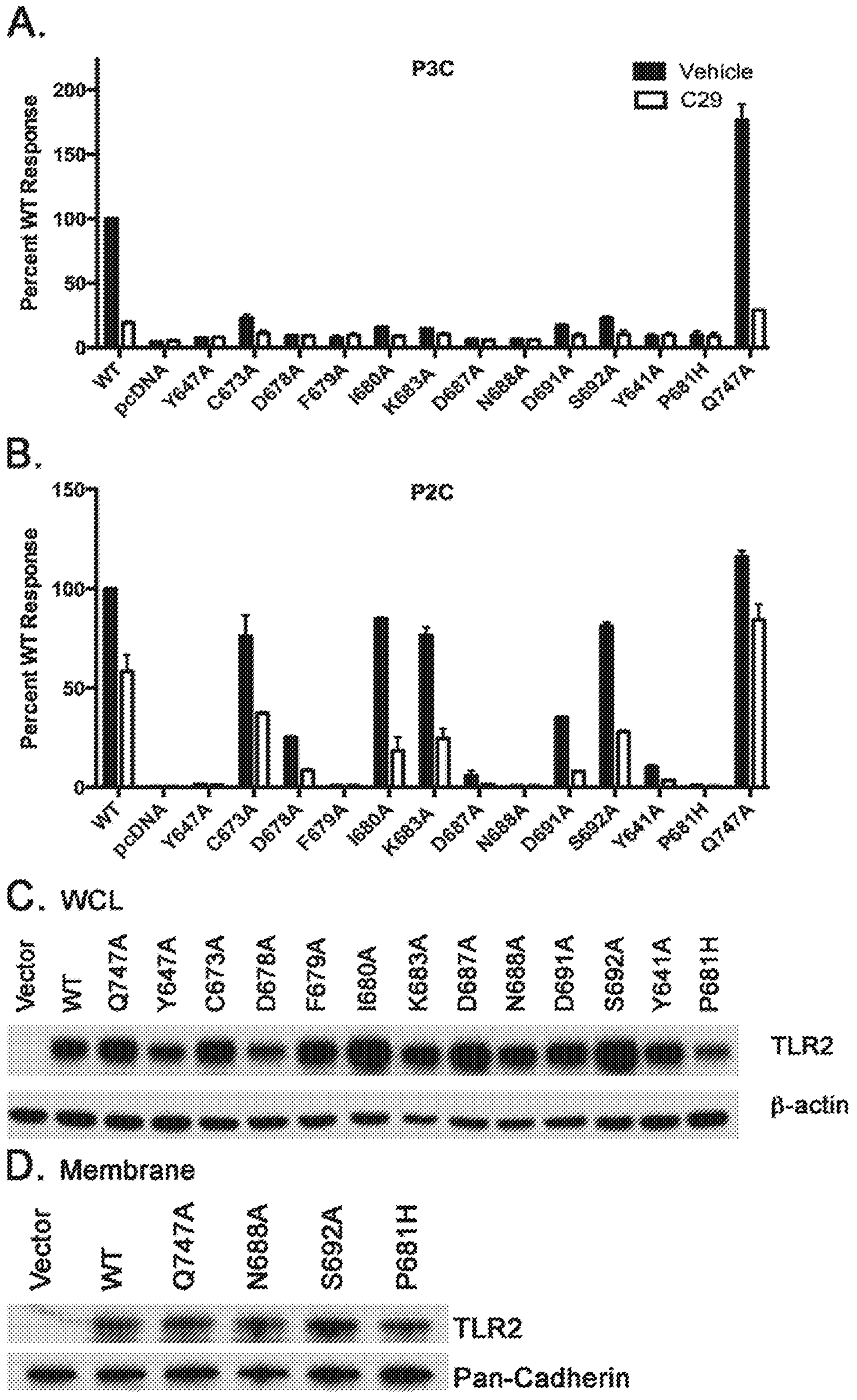
FIG. 3. Pocket residues serve divergent roles in TLR2/1 and TLR2/6 responsiveness. (A, B) HEK293T cells were transiently transfected with reporter constructs for ELAM-luciferase, *Renilla*-luciferase, and either pcDNA3.1, WT pcDNA3-YFP-hTLR2, or mutant TLR2 constructs in the same vector. Cells were pretreated for 1 hr with media, vehicle (65 μM NaOH), or C29 (50 μM) and treated with P3C or P2C (50 ng/mL) for 5 hrs in the presence of media, vehicle, or C29. Lysates were prepared and the dual-luciferase assay performed. (C, D) HEK293T cells were transiently transfected with pcDNA3.1, WT pcDNA3-YFP-hTLR2, or mutant TLR2 constructs in the same vector. Western analysis was performed using whole cell lysates (WCL) (C) or membrane extracts (D) to insure comparable expression of each TLR2 mutant. Pan-Cadherin was probed as a loading protein for membrane extracts. Panels A and B represent the mean±SEM from 2 independent experiments each carried out in duplicate and panels C and D are representative of 2 independent experiments.

Alanine scanning mutagenesis of all 10 BB loop pocket residues was performed as well as three additional mutations Y641A, P681H, and Q747A, and their effect on TLR2/1 and TLR2/6 signaling in the absence or presence of C29 was examined using our NF-κβ reporter assay. Y641A and P681H were shown previously to play a role in the TLR2-MyD88 interaction (Brown V, et al. (2006) *European journal of immunology* 36(3):742-753; Xu Y, et al. (2000) *Nature* 408(6808):111-115) and Gautam et al. reported that Q747 was not important for TLR2 signaling, and therefore, served as a control mutation (Gautam J K, et al. (2006) *The Journal of biological chemistry* 281(40):30132-30142). All 10 BB loop pocket mutants, i.e., including Y647A and P681H, were critical for TLR2/1 signaling (FIG. 3, panel A). Interestingly, the C673A, I680A, K683A, and S692A BB loop pocket mutants retained the ability to signal through TLR2/6, suggesting divergent roles for these amino acids in TLR2/1 and TLR2/6 responsiveness (FIG. 3, panel B). Western analysis revealed that total protein expression of each TLR2 mutant was comparable to that of wild-type TLR2 (FIG. 3, panel C). Importantly, TLR2 signaling-deficient mutants had levels of membrane protein expression similar to wild-type TLR2 (FIG. 3, panel D). These results suggest that human TLR2 BB loop pocket residues are critical for TLR2/1 signaling, but only some are necessary for TLR2/6 signaling.

C29 Derivative, Ortho-Vanillin, Reproduces the TLR2 Inhibitory Activity of C29.

Figure 11:
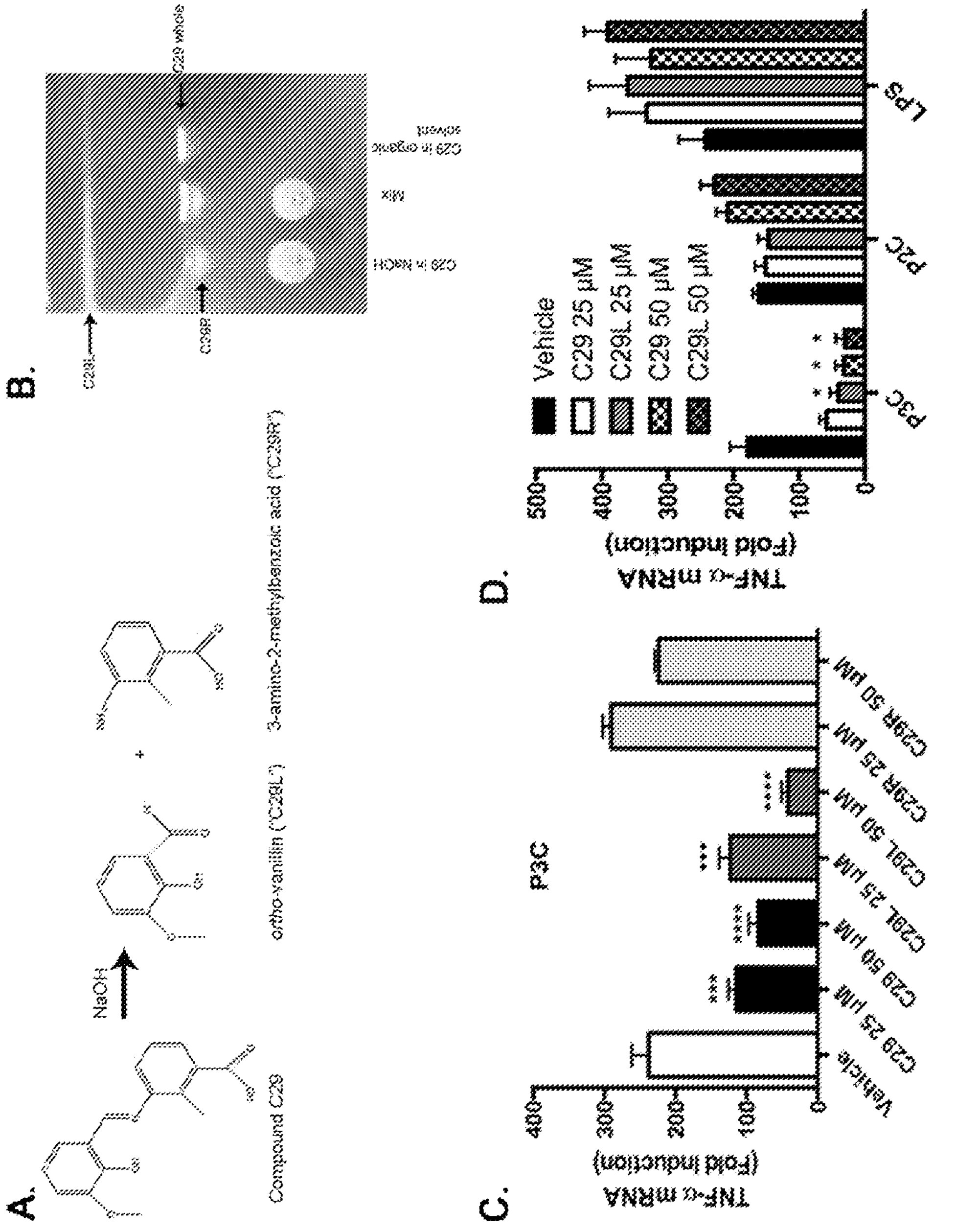
FIG. 11. C29 L reproduces the TLR2 inhibitory activity observed with C29. (A) C29 dissolved in NaOH generates ortho-vanillin ("C29L") and 3-amino-2-methylbenzoic acid ("C29R"). (B) TLC plate coated with silica was spotted with C29 dissolved in 65 μM NaOH, C29 dissolved in ethyl acetate (organic solvent), and a mixture of both. The plate was placed in solvent and visualized using a $KMnO_4$ stain. (C, D) Total RNA was extracted from murine peritoneal macrophages that had been pretreated for 1 hr with vehicle (65 μM NaOH), C29 (25 μM or 50 μM), C29L (25 μM or 50 μM), or C29R (25 μM or 50 μM) and then stimulated with P3C (50 ng/mL), P2C (100 ng/mL), or LPS (100 ng/mL) for 1 hr in the presence of vehicle, C29, C29L, or C29R. TNF-α mRNA was measured as described in FIG. 1, panel D. Quantitative real-time results are representative of 2 independent experiments each carried out in duplicate (*, p≤0.05; , p≤0.01; *, p≤0.001; ****, p≤0.0001).
Figure 12:
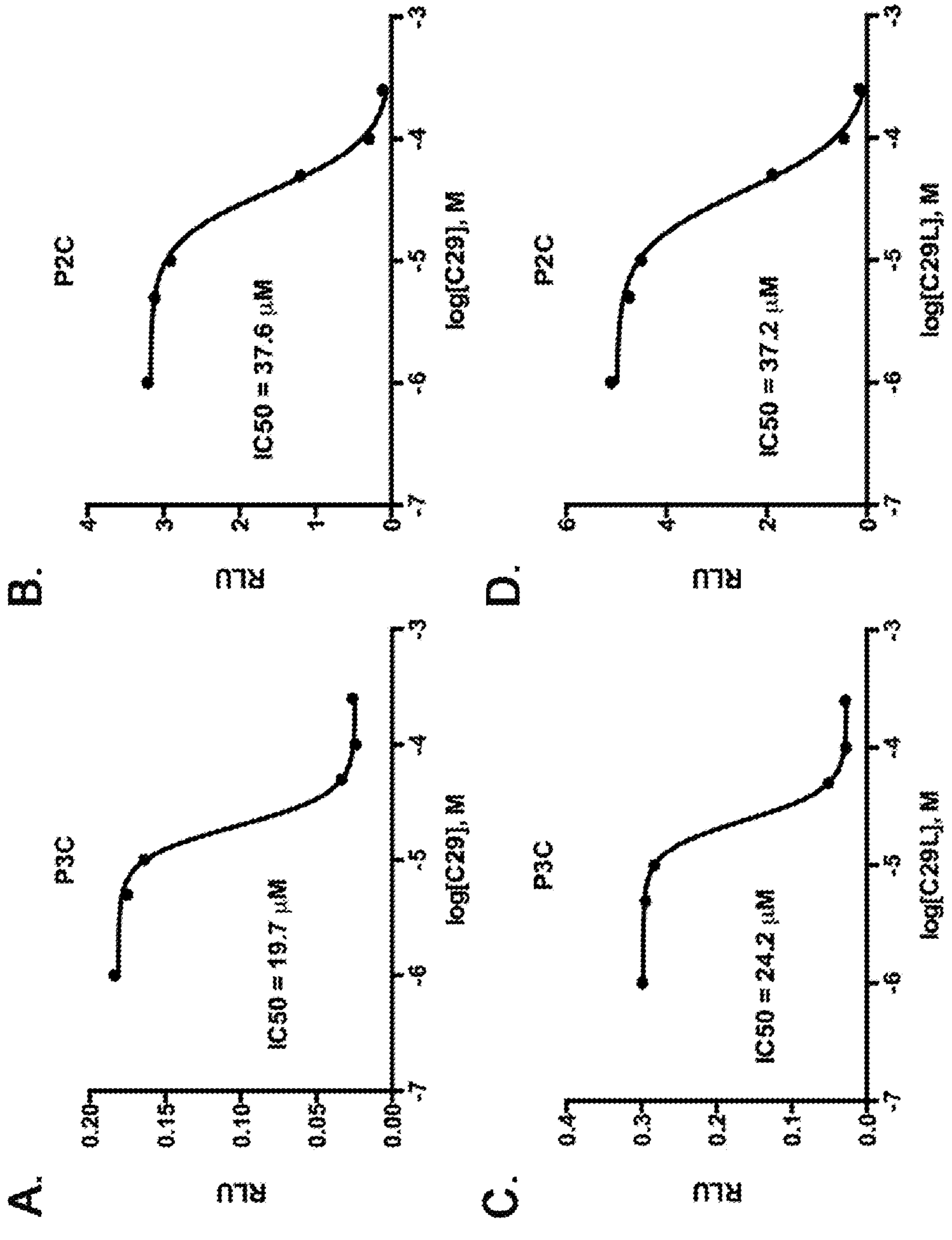
FIG. 12. C29 L blocks human TLR2/1 and TLR2/6 signaling comparably to C29 in HEK293T cells. (A-D) HEK293T cells were transiently transfected with reporter constructs for ELAM-luciferase, *Renilla*-luciferase, and pcDNA3-YFP-hTLR2. Cells were pretreated for 1 hr with C29 or C29L (1 μM-250 μM) and treated with P3C or P2C (50 ng/mL) for 5 hrs in the presence of C29 or C29L. Lysates were prepared and dual-luciferase assay performed. Data is representative of 2 independent experiments each carried out in duplicate.

To preclude cytotoxicity from DMSO, C29 was dissolved in 65 μM NaOH in $H_2O$. The structure of C29 (FIG. 1, panel A) suggested that the imine linkage would likely be highly susceptible to nucleophilic cleavage into two species, consisting of 3-amino-2-methylbenzoic acid ("C29R") and ortho-vanillin ("C29L") (FIG. 11, panel A). Thin layer chromatography confirmed that C29 is cleaved into these two species when dissolved in 65 μM NaOH, but not when dissolved in an organic solvent (FIG. 11, panel B). The two cleavage products, C29L and C29R, were tested to determine if either would reproduce the TLR2 inhibitory activity of C29. C29L, but not C29R, dose-dependently inhibited TLR2/1-induced TNF-α gene expression in murine macrophages while having no effect on TLR2/6 or TLR4 signaling pathways (FIG. 11, panel C and D).

It was next examined if C29L also blocks human TLR2 signaling with similar potency and specificity. Using the NF-κβ reporter assay in HEK293T cells, the 50% inhibitory concentration ($IC_{50}$) of C29 and C29L for human TLR2/1 and TLR2/6 signaling was quantified. C29L blocked hTLR2/1 ($IC_{50}$=24.2 μM) and hTLR2/6 signaling ($IC_{50}$=37.2 μM) comparably to C29 ($IC_{50}$=19.7 μM and 37.6 μM) (FIG. S8).

Figure 13:
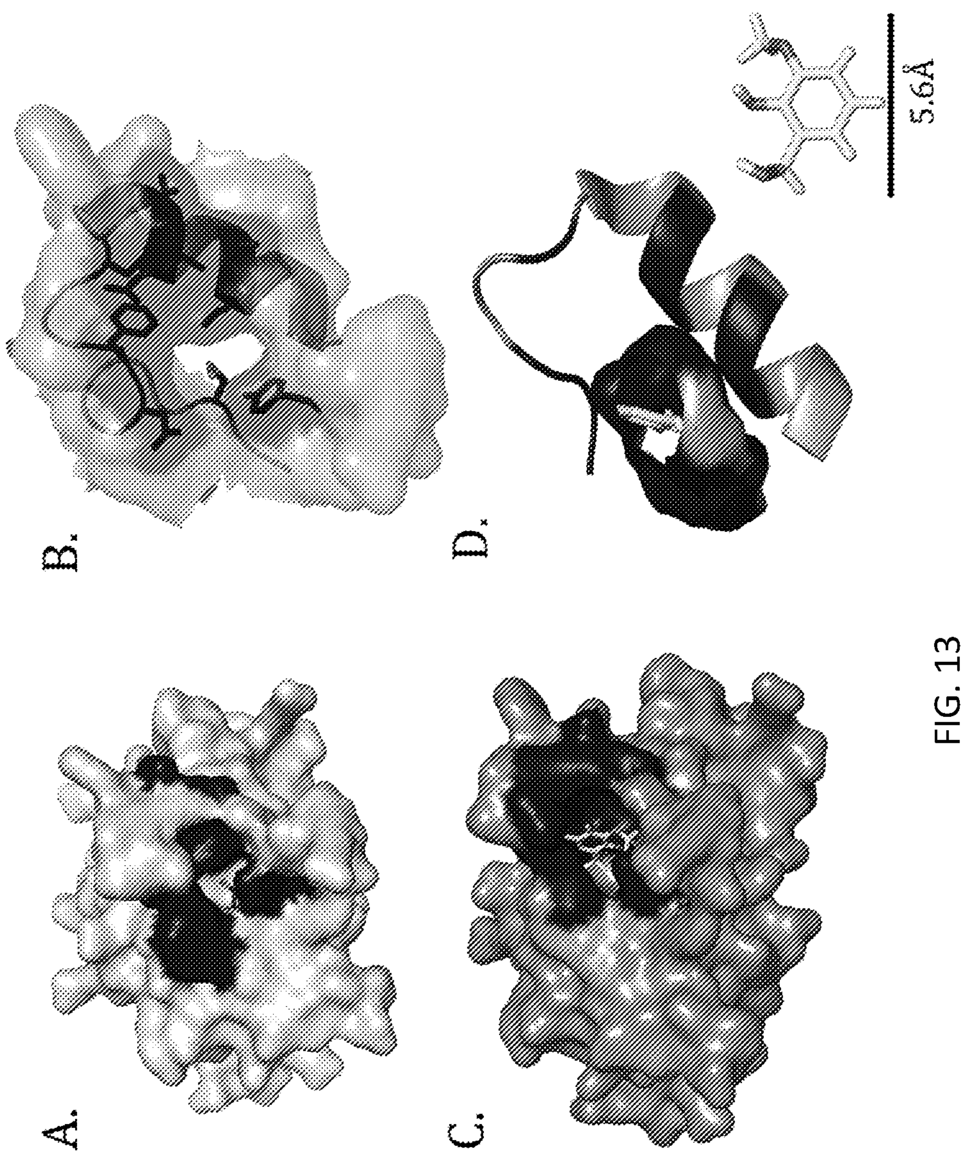
FIG. 13. Surface representation of the BB loop pocket modeled with C29L. (A) Surface representation of the BB loop pocket. Residues Y647, C673, D678, F679, I680, K683, D687, N688, D691, and S692 that comprise the BB loop pocket are highlighted. (B) Close-up depiction of the BB loop pocket showing both surface representation and underlying secondary structure and the BB loop pocket residues (highlighted). (C, D) Surface representation of the solvent accessible BB loop pocket with C29L modeled into this pocket (Lower right depicts C29L with carbon, oxygen, and hydrogen atoms.

Modeling of the BB loop pocket and C29L revealed that C29L fits within the BB loop pocket (FIG. 13). Together, these hypothetical predictions suggest that C29L is comparable to C29 for inhibiting human and murine TLR2 signaling.

C29L Inhibits TLR2/1-Induced Inflammation In Vivo.

Figure 4:
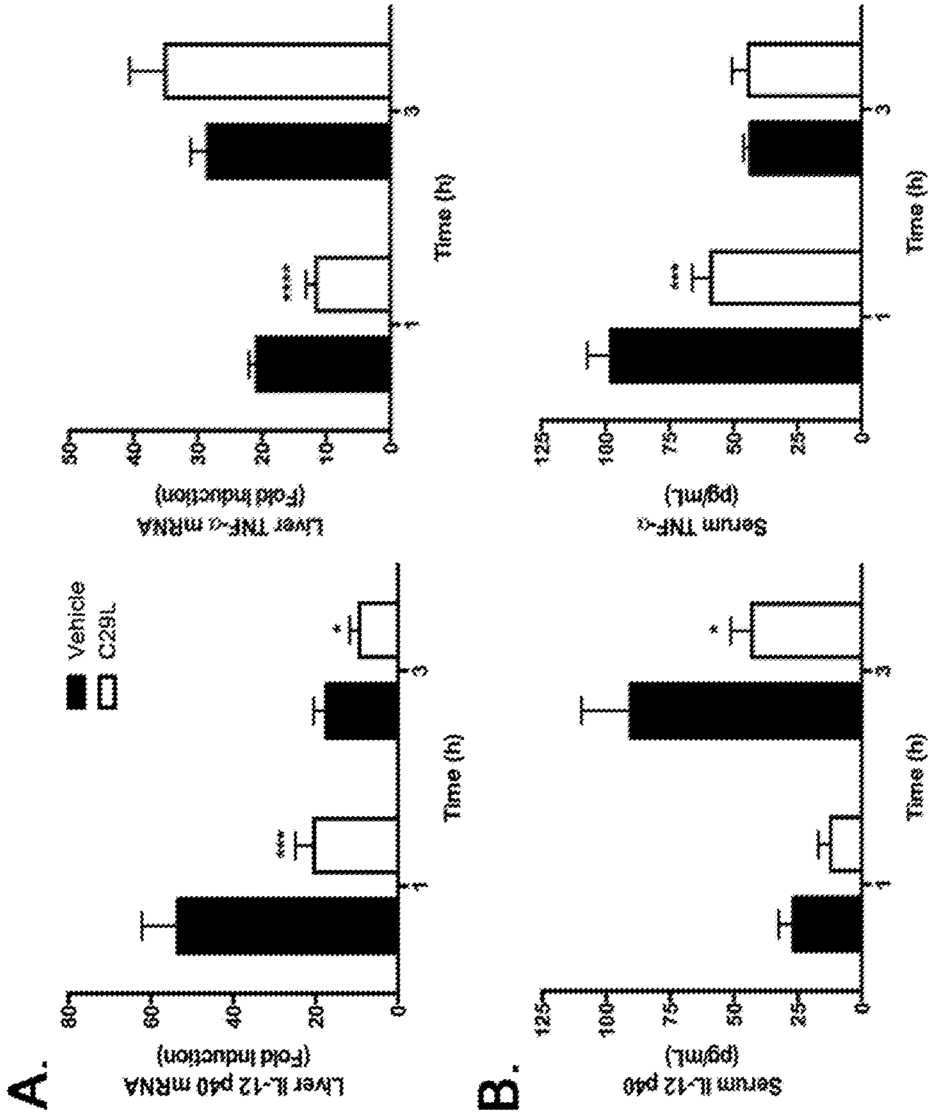
FIG. 4. C29L inhibits TLR2/1-induced inflammation in vivo. C57BL/6J mice were pretreated i.p. with vehicle (water) or C29L (1.314 mM/g) for 1 hr. Mice received a second pretreatment i.p. with vehicle (water) or C29L (1.314 mM/g) and subsequently were challenged i.p. with PBS or P3C (100 μg) and sacrificed 1 hr or 3 hrs later. Liver RNA (A) was analyzed by qRT-PCR and serum concentrations (B) were analyzed by Multiplex (*, p≤0.05; *, p≤0.001; **, p≤0.0001). Panels A and B, n=6 (the combined data from two separate experiments) for each treatment group.

One of the advantages of using C29L in vivo is that C29L is more soluble in water than C29. It was next examined if C29L could inhibit TLR2/1-induced proinflammatory cytokine in vivo. Mice treated twice with C29L prior to administration of P3C significantly blocked IL-12 p40 and TNF-α liver cytokine mRNA and serum protein (FIG. 4). Importantly, C29L had a significant inhibitory effect at the later time point for IL-12 p40. Collectively, C29L blocks TLR2/1 signaling both in vitro and in vivo.

Materials and Methods

CADD In Silico Screening.

CADD screening was performed as described previously (Hancock C N, et al. (2005) *Journal of medicinal chemistry* 48(14):4586-4595; Li T, et al. (2014) *Human molecular genetics* 23(23):6212-6222; Zhong S, et al. (2008) *Journal of medicinal chemistry* 51(15):4553-4562) to identify small molecule inhibitors of TLR2 signaling. Briefly, CADD analysis required the following steps, i.e., visual identification of a putative "pocket" in the 3D structure of the TLR2 TIR domain (FIG. 5, panel A), primary docking using DOCK (Kuntz I D, et al. (1982) *Journal of molecular biology* 161(2):269-288) of more than one million low molecular weight, commercially available and FDA-approved compounds, a more rigorous secondary docking of various conformations of TLR2 obtained from molecular dynamics simulation of the protein using CHARMM (Brooks B R, et al. (2009) *Journal of computational chemistry* 30(10):1545-1614), and screening the top 149 and 20 FDA-approved drugs for the ability to block TLR2 signaling in stably or transiently transfected HEK-TLR2 cells, THP-1 cells, or murine macrophages as described below.

Quantitative Real-Time PCR (qRT-PCR).

Cytokine gene expression was measured by qRT-PCR with transcript-specific primers using SYBR Green in the ABI Prism 7900 Fast Real Time PCR system (Applied Biosystems, Foster City, CA) as described (Cole L E, et al. (2006) *Journal of immunology* 176(11):6888-6899).

Transient Transfection and NF-κβ Reporter Assay.

HEK293T cells were cultured and plated overnight in 12-well tissue culture plates ($2\times10^5$ cells/well). Transfection mixtures consisted of pcDNA3-YFP-hTLR2 or pcDNA3.1 control vector (1 μg/well each), pELAM (NF-κB)-luciferase (0.2 μg/well), and pRL-TK-*Renilla* luciferase (0.05 μg/well). Transfection was carried out using Superfect transfection reagent, cells were recovered for 48 h, and treated for 5 h with medium or stimuli in the presence/absence of C29. Cells were lysed in a passive lysis buffer (Promega, Madison, WI) and firefly luciferase and *Renilla* luciferase activities were measured using the dual luciferase reporter assay system (Promega, Madison, WI). *Renilla* luciferase was used for normalization and all values were further standardized to medium-treated pcDNA3-YFP-hTLR2 transfectants to determine relative luciferase units (RLU) (Singh I S, et al. (2008) *American journal of respiratory cell and molecular biology* 39(2):235-242).

Cytokine Protein Measurements.

Cytokine levels in culture supernatants were analyzed by Multiplex beads in the Cytokine Core Laboratory (UMB).

In Vivo Studies of TLR2 Inhibitor.

All animal studies were carried out with institutional approval. Female C57BL/6J mice (6-8 weeks old) were purchased from The Jackson Laboratory (Bar Harbor, ME) and (n=3 mice/group) received PBS, $H_2O$, or C29L (in $H_2O$) i.p. (1.314 mM/g). After 1 h, mice received a second injection of PBS, $H_2O$, or C29L i.p. (1.314 mM/g) and were subsequently challenged i.p. with PBS or P3C (100 μg) for 1 or 3 h. Mice were bled and sera was prepared. Livers were also extracted for qRT-PCR analysis.

CADD In Silico Screening.

In silico screening using CADD followed a previously described protocol (Hancock C N, et al. (2005) *Journal of medicinal chemistry* 48(14):4586-4595) adjusted for the present target, the TLR2 TIR domain. The 3D structure of the human TLR2 TIR domain was retrieved from the Protein DataBank (ID: 1FYW). Charges and hydrogens were added using SYBYL6.4 (Tripos, Inc.). All docking calculations were carried out with DOCK (Kuntz I D, et al. (1982) *Journal of molecular biology* 161(2):269-288) using flexible ligands based on the anchored search method (Kuntz I D (1992) *Science* 257(5073):1078-1082). The solvent accessible surface (Connolly M L (1983) *Science* 221(4612):709-713) was calculated with the program DMS (Ferrin T E, et al. (1988) *J Mol. Graphics* 6(1):13-27) using a surface density of 2.76 surface points per $Å^2$ and a probe radius of 1.4 $Å^2$. Sphere sets were calculated with the DOCK-associated program SPHGEN. From the full sphere set, sphere clusters in the TLR2 TIR putative "pocket" were identified, where the pocket is adjacent to the BB loop with the conserved PG pair and is comprised of residues Y641, C673, D678, F679, I680, K683, D687, N688, D691, and S692. The selected sphere set acted as the basis for initial ligand placement during database searching. The GRID method (Goodford P J (1984) *J Med Chem* 27(5):558-564) within DOCK was used to approximate the ligand-receptor interaction energy during ligand placement by the sum of the electrostatic and van der Waals (vdW) components. The GRID box dimensions were 41.2×41.7×41.6 $Å^3$ centered around the sphere set to ensure that docked molecules were within the grid.

A database of more than 1 million low molecular weight, commercially available and FDA-approved compounds was used for the initial virtual screening. These databases were created by converting files obtained from the vendors in the 2D SDF format to the 3D MOL2 format through a procedure that included geometry generation, addition of hydrogens and charges, and force field optimization using SYBYL6.4 along with in-house programs (Huang N, et al. (2004) *Journal of medicinal chemistry* 47(14):3502-3511; Pan Y, et al. (2003) *Journal of chemical information and computer sciences* 43(1):267-272). The compounds screened in this manner had between 10 and 40 heavy atoms and less than 10 rotatable bonds. During the docking procedure, each compound was divided into non-overlapping rigid segments connected by rotatable bonds. Segments with more than five heavy atoms were used as anchors, each of which was docked into the binding site in 250 orientations and minimized. The remainder of the molecule was built around the anchor in stepwise fashion by adding other segments connected through rotatable bonds. At each step, the dihedral of the rotatable bond was sampled in increments of 10° and the lowest energy conformation was selected. During primary docking, each rotatable bond was minimized as it was created without reminimizing the other bonds. Pruning of the conformational orientations ensured conformational diversity and more favorable energies (Ewing T J, Kuntz I D (1997) *J. Comput. Chem* 18(9):1175-1189; Leach A R, Kuntz I D (1992) *J. Comput. Chem* 13(6):730-748). Energy scoring was performed with a distant-dependent dielectric, with a dielectric constant of 4, and using an all atom model. Once the whole molecule was built, then it was minimized. The conformation of each molecule with the most favorable interaction energy was selected and saved.

After the primary docking, compounds were chosen for the secondary screening based on their normalized vdW attractive interaction energy scores. Compound selection based on the DOCK energy score favors compounds with higher molecular weight (MW) since MW contributes to the energy score. To minimize this size bias, an efficient procedure by which the DOCK energies are normalized by the number of heavy atoms N or by a power of N was applied (Pan Y, et al. (2003) *Journal of chemical information and computer sciences* 43(1):267-272). $IE_{norm,vdW}=IE_{vdW}/N^x$. Normalization of the vdW attractive energies was done with x=1, 0.33, 0.5, and 0.67 and the MW distributions of the top 50,000 compounds in each category were analyzed, with x=0.33 normalization used for the selection of compounds for secondary screening.

The top 50,000 compounds were subjected to a more rigorous and computationally expensive docking procedure, referred to as secondary database screening. The procedure described for primary docking was followed with the additional step of minimizing all rotatable bonds simultaneously during the stepwise building of the molecule. In addition, the docking was performed against the crystal conformation and 3 additional conformations of TLR2 obtained from a molecular dynamics (MD) simulations of the protein. The MD simulation was performed with the program CHARMM (Brooks B R, et al. (2009) *Journal of computational chemistry* 30(10):1545-1614) using the CHARMM22/CMAP force field (MacKerell A D, Jr., et al. (1998) *Encyclopedia of Computational Chemistry*, eds Schleyer P v R, Allinger N L, Clark T, Gasteiger J, Kollman P A, Schaefer H F, III, & Schreiner P R (John Wiley & Sons, Chichester), Vol 1, pp 271-277; MacKerell A D, Jr., Feig M, & Brooks C L, III (2004) *J. Am. Chem. Soc.* 126:698-699; MacKerell A D, Jr., Feig M, & Brooks C L, III (2004) *J. Comp. Chem.* 25:1400-1415) with the TIP3P water model (Jorgensen W L, et al. (1983) *Journal of Chemical Physics* 79:926-935) using periodic boundary conditions. The periodic system was a truncated octahedral of dimensions 86.2 Å with the protein centered in the simulation box. Two sodium ions were included to yield a neutral system. Electrostatic interactions were treated using particle mesh Ewald and the Lennard Jones (LJ) interactions were truncated over 8 to 10 Å using force switching (Steinbach P J & Brooks B R (1994) *J. Comp. Chem.* 15:667-683); non-bond interaction lists were updated heuristically out to 12 Å. Following overlay of the TLR2 protein with water the system was subjected to a 500 step Steepest Descent minimization following which the 5 ns production MD simulation was performed at 298 K using the leap frog integrator with a time step of 2 fs, and SHAKE to constrain all covalent bonds involving hydrogen atoms (Ryckaert J P, Ciccotti G, & Berendsen H J C (1977) *J. Comp. Phys.* 23:327-341). Coordinates were saved every 1 ns for analysis. Final conformations for docking were selected by root-mean-square difference clustering with NMRCLUST (Kelley L A, Gardner S P, & Sutcliffe M J (1996) *Protein Eng.* 9:1063-1065) on structures from 2 to 5 ns of the MD simulations with representative structures from the three largest clusters selected for secondary docking. For each compound the most favorable total interaction energies from the four protein conformations was used for final ranking from which the top 1000 compounds were selected and subjected to chemical diversity analysis. Of these, 149 compounds were selected based on chemical diversity and physicochemical properties appropriate for bioavailability (Lipinski C A (2000) *Journal of pharmacological and toxicological methods* 44(1):235-249) and 20 FDA-approved drugs for the ability to block TLR2 signaling.

Reagents.

Protein-free LPS from *Escherichia coli* K235 (<0.008%) was prepared as a modification of McIntire et al. (McIntire F C, et al. (1967) *Biochemistry* 6(8):2363-2372). P3C and P2C were purchased from EMC Microcollections GmbH (Tuebingen, Germany). Recombinant mouse and human TNF-α were purchased from eBioscience (San Diego, CA). *Francisella tularensis* LVS and *Streptococcus pneumoniae* were grown as previously described (Cole L E, et al. (2006) *Journal of immunology* 176(11):6888-6899, Pennini M E, et al. (2013) *Journal of immunology* 190(1):307-316). Heat-killed *Streptococcus pneumoniae*, heat-killed *Pseudomonas aeruginosa*, heat-killed *Staphylococcus aureus, S. aureus* lipoteichoic acid, zymosan, poly(I:C), R848, and CpG ODN 1668 were purchased from Invivogen (San Diego, CA). QuikChange Lightning Site-Directed Mutagenesis Kit was purchased from Agilent Technologies (Santa Clara, CA). *Escherichia coli* was purchased from Life Technologies (Carlsbad, CA) and heat-killed by heating at 60° C. for 60 min. 3-[[2-hydroxy-3-methoxyphenyl)methylene]amino]-2-methylbenzoic acid (C29) was purchased from ChemDiv (San Diego, CA). ortho-vanillin and 3-amino-2-methylbenzoic acid were purchased from Oakwood (West Columbia, SC). Additional compounds were purchased from Chembridge (San Diego, CA), Ambinter (Orléans, France), and Ryan Scientific (Mount Pleasant, SC). Abs directed against phospho-ERK 1/2, phospho-p38, phospho-JNK 1/2, phospho-p65, IκBα, β-actin, MyD88, and Pan-Cadherin were purchased from Cell Signaling Technology (Danvers, MA). Anti-human TLR2 Ab was obtained from Abcam (Cambridge, MA).

Cell Culture.

Peritoneal exudate macrophages were obtained by peritoneal lavage from 6-8 week old C57BL/6J mice (The Jackson Laboratory, Bar Harbor, ME) 4 days after i.p. injection with sterile thioglycollate (Remel) as described (Salkowski C A, et al. (1999) *Journal of immunology* 163(3):1529-1536). Macrophages were washed and cultured in RPMI 1640 supplemented with 2% FBS, 2 mM glutamine, 1% penicillin and streptomycin, as described (Salkowski C A, et al. (1999) *Journal of immunology* 163(3):1529-1536). Macrophages were plated in 6-well tissue culture dishes ($4\times10^6$ cells/well) or in 12-well tissue culture dishes ($2\times10^6$ cells/well). After overnight incubation to allow for adherence of macrophages, cells were treated with the indicated stimuli.

Non-transfected HEK293T cells were maintained in Dulbecco's Modified Eagle Medium (DMEM) supplemented with 10% FBS, 2 mM glutamine, 1% penicillin and streptomycin. HEK293T cells stably transfected to express human TLR2-YFP (HEK-TLR2), kindly provided by Dr. Douglas Golenbock (University of Massachusetts Medical School), were enriched in DMEM supplemented with 10% FBS, 2 mM glutamine, 10 μg/mL ciprofloxacin, and 5 mg/mL G418 Geneticin. THP-1 cells (ATCC, Manassas, VA) were cultured in RPMI 1640 medium modified to contain 2 mM L-glutamine, 10 mM HEPES, 1 mM sodium pyruvate, 4500 mg/L glucose, 1500 mg/L sodium bicarbonate and supplemented with 10% heat-inactivated FBS. THP-1 cells were plated at $2\times10^6$ cells/well in 12-well tissue culture plates. Cells were cultured with 20 ng/mL PMA for 24 hrs. Adherent cells were washed twice with THP-1 medium and then treated.

Recombinant Plasmids and Site-Directed Mutagenesis.

pcDNA3-YFP-hTLR2 was described previously (Xiong Y, et al. (2012) *The Journal of biological chemistry* 287(45): 38327-38337). The NF-κβ-responsive reporter plasmid, pELAM-Luc, was kindly provided by Dr. Douglas Golenbock (University of Massachusetts Medical School). pRL-TK-*Renilla* luciferase was obtained from Promega (Madison, WI) and pcDNA3.1 was purchased from Invitrogen (Carlsbad, CA). pcDNA3-CFP-hTLR6 and pFLAG-CMV1-hTLR1 were kind gifts from Dr. Andrei Medvedev (University of Connecticut Health Center). pcDNA3.1-mTLR2-CFP, pcDNA3.1-mTLR1-YFP, and pcDNA3.1-mTLR6-CFP plasmids were provided by Dr. Vladimir Toshchakov (University of Maryland, School of Medicine).

The TLR2 BB loop pocket mutations were introduced into the pcDNA3-YFP-hTLR2 vector using the QuikChange Lightning Site-Directed Mutagenesis Kit (Agilent Technologies) according to the manufacturer's instructions and the mutation was verified by sequencing.

Preparation of Cell Membrane Fractions.

HEK293T cells were transiently transfected with pcDNA3.1, WT pcDNA3-YFP-hTLR2, or mutant TLR2 constructs in the same vector. Forty-eight hours post-transfection cells were resuspended in homogenization buffer, lysed, and membrane fractions were prepared as described previously (Bhat N, et al. (1999) *Journal of immunology* 162(12):7335-7342).

Co-Immunoprecipitation and Immunoblotting.

Cells were treated and washed once with 1×PBS and lysed using buffer containing 20 mM HEPES (pH 7.4), 150 mM NaCl, 1 mM EDTA, 1 mM EGTA (pH 8.0), 50 mM NaF, 0.5% Triton X-100, 1 mM $Na_3VO_4$, 1 mM DTT, 1 mM PMSF, and protease inhibitor (Roche Applied Science, Indianapolis, IN). Cells were harvested and protein was quantified using BCA Protein assay reagents (Thermo Scientific/Pierce, Rockford, IL). Whole cell lysates (500 μg/500 μL) were precleared using 10 μL of pre-washed Protein G Agarose (Roche Applied Science, Indianapolis, IN) for 2 hours at 4° C. with rotation. Precleared samples were incubated with the respective antibody and rotated overnight at 4° C. Pre-washed Protein G (40 μL) was added to each sample and rotated for 4 h at 4° C. Beads were washed three times in lysis buffer (without protease inhibitor) and finally in complete lysis buffer. Beads were resuspended in 2× Laemmli Sample Buffer and boiled for 10 min. Immunoprecipitated proteins were separated by 10% SDS-PAGE, transferred onto a polyvinylidene difluoride membrane, blocked, incubated with respective primary and secondary antibodies, and bands were visualized using ECL Plus reagents (Amersham Pharmacia Biotech, Piscataway, NJ), as described (Polumuri S K, et al. (2012) *Journal of immunology* 189(1):50-60).

Evaluation of Cellular Cytotoxicity.

Cellular cytotoxicity was determined by measuring lactate dehydrogenase (LDH) activity released in the media after treatment with TLR agonist or TNF-α in the presence of media, vehicle (NaOH), or C29 using the CytoTox 96 nonradioactive cytotoxicity assay (Promega, Madison, WI) and quantified by measuring wavelength absorbance at 490 nm. Treatment of cells with Triton X-100 served as the positive control.

Statistical Analysis.

One-way ANOVA with Tukey's multiple comparisons post-hoc test was used to determine statistical significance ($p$ values$<0.05$) using GraphPad Prism 6.0 (GraphPad Software Inc., San Diego, CA). Values are represented as the mean±SEM.

Discussion

TLR activation involves multifaceted interactions of cytoplasmic TIR domain containing proteins. The BB loop has been established as central for mediating TIR domain interactions. Mutagenesis of TLR2 BB loop residues and cell-permeating decoy peptides that target this region have revealed the functional importance of the BB loop in mediating downstream signaling (Brown V, et al. (2006) *European journal of immunology* 36(3):742-753, Underhill D M, et al. (1999) *Nature* 401(6755):811-815; Underhill D M, et al. (1999) *Proceedings of the National Academy of Sciences of the United States of America* 96(25):14459-14463; Xu Y, et al. (2000) *Nature* 408(6808):111-115, Toshchakov V Y, et al. (2007) *Journal of immunology* 178(5):2655-2660). In the study shown herein, in silico screening targeting a novel TLR2 BB loop pocket was combined with biological screening in various cell types to identify C29 and a derivative, o-vanillin, as inhibitors of both murine and human TLR2 signaling in response to synthetic or bacterial agonists.

In human TLR2 signaling, C29 and o-vanillin blocked both the TLR2/1 and TLR2/6 pathways (FIGS. 1, 8, 9, 10 (panel C), and 12), although the percent inhibition in HEK-TLR2 cells was consistently greater when TLR2/1 is stimulated (FIGS. 1 (panel B), 3, 8, 9, 10 (panel C), and 12). In murine cells, C29 and o-vanillin block only the TLR2/1 pathway significantly (FIGS. 1, 10, and 11). This was confirmed using *S. aureus* LTA, a TLR2/1 ligand (Han S H, et al. (2003) *Infection and immunity* 71(10):5541-5548; Travassos L H, et al. (2004) *EMBO reports* 5(10):1000-1006), while C29 failed to block proinflammatory gene expression induced by zymosan (FIG. 10), a TLR2/6 agonist (Ozinsky A, et al. (2000) *Proceedings of the National Academy of Sciences of the United States of America* 97(25): 13766-13771). The results herein support a previous study showing that cell-permeating decoy peptides derived from the BB loop of the TLR2 TIR domain inhibited ERK activation induced by P3C, but not P2C, in murine macrophages (Toshchakov V Y, et al. (2007) *Journal of immunology* 178(5):2655-2660).

Figure 14:
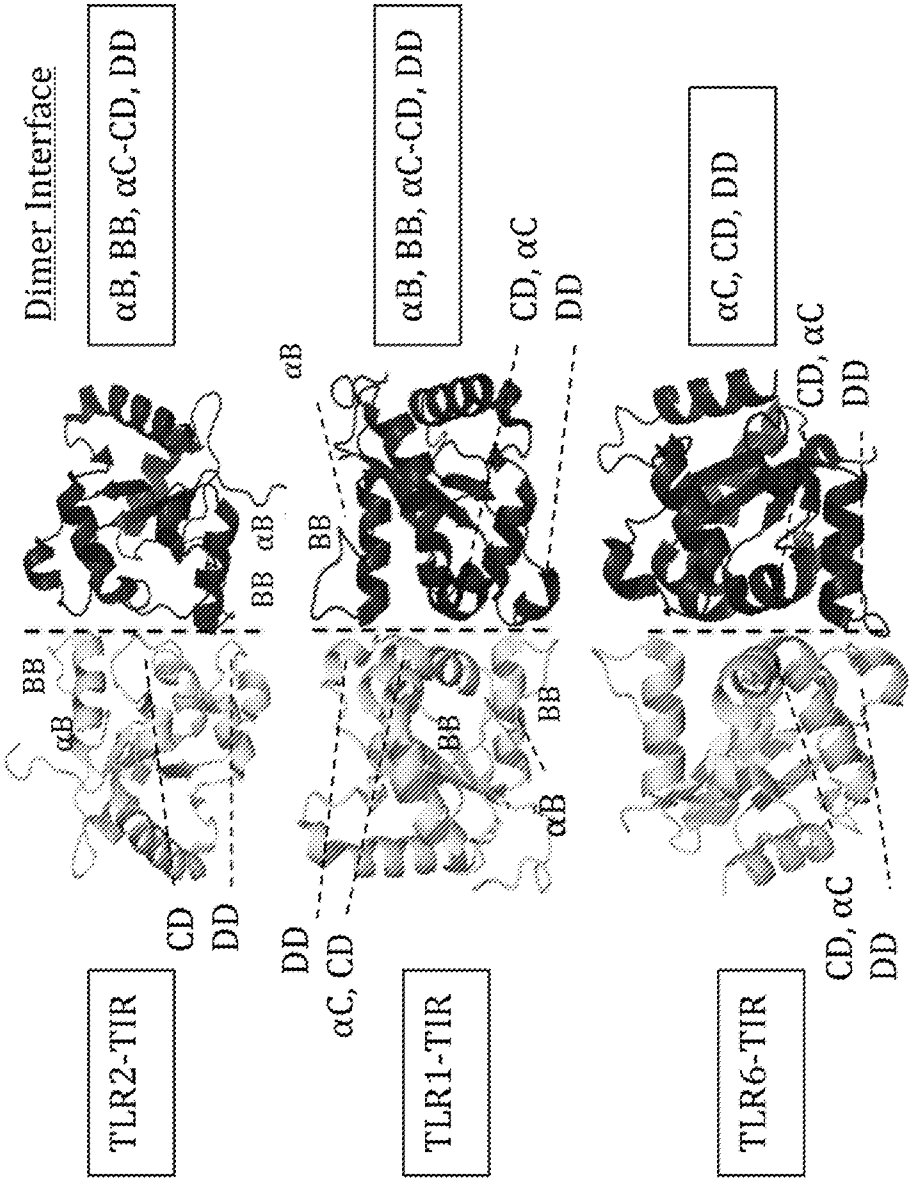
FIG. 14. Cartoon representation of the homodimeric interactions observed in the crystal structures of TIR1 (PDB ID: 1FYV), TIR2 (PDB ID: 1FYW), and TIR6 (PDB ID: 4OM7)

A possible explanation for this difference in C29-mediated inhibition for human versus murine TLR2 signaling could be that the BB loops of murine and human TLR2 play distinct roles in heterodimer formation and MyD88 recruitment. The highly flexible BB loop is central to many molecular interactions involving TIR domains and adopts different conformations as observed in functional and structural studies of TLR1, TLR2, TLR10, and recently, TLR6 (Xu Y, et al. (2000) *Nature* 408(6808):111-115; Gautam J K, et al. (2006) *The Journal of biological chemistry* 281(40): 30132-30142; Jang T H & Park H H (2014) *Journal of molecular biology* 426(19):3305-3313; Nyman T, et al. (2008) *The Journal of biological chemistry* 283(18):11861-11865; Tao X, et al. (2002) *Biochemical and biophysical research communications* 299(2):216-221). Homodimeric molecular interactions observed in structural studies of human TLR1, TLR2, and TLR10 are largely mediated by residues found on the BB loop, DD loop, and αC-helix (Xu Y, et al. (2000) *Nature* 408(6808):111-115; Gautam J K, et al. (2006) *The Journal of biological chemistry* 281(40): 30132-30142; Nyman T, et al. (2008) *The Journal of biological chemistry* 283(18):11861-11865; Tao X, et al. (2002) *Biochemical and biophysical research communications* 299 (2):216-221) (FIG. 14). In contrast, homodimeric molecular interactions observed in the recent crystal structure of the TLR6 TIR domain (Jang T H & Park H H (2014) *Journal of molecular biology* 426(19):3305-3313) are reported not to include BB loop interactions, but rather, involve CD loop, DD loop, and the αC helix residues (FIG. 14). This may explain why a proportionally greater inhibitory effect of C29 or o-vanillin on hTLR2/1 signaling compared to hTLR2/6 signaling and a minimal effect on mTLR2/6 signaling was observed. Analysis of the BB loop pocket mutants further supports that BB loop pocket residues are highly critical for TLR2/1 signaling, while only C673, I680, K683, S692 are indispensable for TLR2/6 signaling (FIG. 3, panels A and B).

Based on the functional mutagenesis data, C29 and o-vanillin may function by specifically targeting the BB loop pocket of the TLR2 TIR domain, altering its function and/or position. Jiang et al. described a murine mutation in MyD88 (I179N), called Pococurante (Poc), that exhibited deficient TLR2/1 signaling, but normal TLR2/6 signaling, suggesting that TLR2 interacts with MyD88 in different ways (Jiang Z, et al. (2006) *Proceedings of the National Academy of Sciences of the United States of America* 103(29):10961-10966). Using molecular dynamic simulations, Snyder et al. demonstrated that in wild-type MyD88, the BB loop is stabilized, whereas the Poc mutation potentiates its flexibility (Snyder G A, et al. (2013) *Proceedings of the National Academy of Sciences of the United States of America* 110 (17):6985-6990). A mobile BB loop could potentially result in a greater entropic cost to obtain stable TIR:TIR interactions and lead to deficient signaling (Snyder G A, et al. (2013) *Proceedings of the National Academy of Sciences of the United States of America* 110(17):6985-6990). Differences observed in C29- and o-vanillin-mediated inhibition of human and murine TLR2 signaling and mutagenesis studies of BB loop pocket residues may reflect differential use of the BB loop involving TIR1, TIR2, TIR6, and MyD88 molecular interactions. Future structural studies involving bona fide heterodimers of TLR1/2 and TLR2/6 TIR domain would be very helpful in understanding the differences in TLR2/1 and TLR2/6 signaling.

Finally, it was sought to determine if o-vanillin would inhibit TLR2-mediated induction of proinflammatory cytokines in vivo. O-vanillin is more soluble in water than C29 and, therefore, was used in the animal studies provided herein. Mice pretreated twice with o-vanillin and challenged with P3C showed reduced IL-12 p40 and TNF-α liver mRNA and serum protein compared to mice pretreated with vehicle control ($H_2O$) (FIG. 4). One of the limitations of using o-vanillin in vivo is its poor bioavailability, as has been reported previously for its isomer, vanillin (Beaudry F, et al. (2010) *Phytotherapy research: PTR* 24(4):525-530). Due to this challenge, a high dose was administered twice to achieve an appreciable inhibitory effect in vivo. Despite this drawback, it was possible to measure a significant inhibitory effect for IL-12 p40 at the later time point (FIG. 4). Future studies will focus on chemical modification of o-vanillin to increase its inhibitory efficacy and/or deliver it on a carrier to reduce rapid clearance. A polymeric pro-drug of vanillin was found to reduce acetaminophen-induced liver injury in mice (Kwon J, et al. (2013) *Biomacromolecules* 14(5):1618-1626). With the increasing knowledge of the crystal structures of the different TLR family members and sites of protein-protein interactions, CADD could potentially lead to targeted therapeutics against other TLR family members.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. A method of treating an inflammatory disease or condition in a subject consisting of administering to the subject a therapeutically effective amount of a compound selected from the group consisting of C29, ortho-vanillin, a salt of C29, a solvate of C29, a hydrate of C29, a prodrug of C29, a salt of ortho-vanillin, a solvate of ortho-vanillin, a hydrate of ortho-vanillin, a prodrug of ortho-vanillin, and a combination thereof, wherein the compound is administered in a composition comprising a pharmaceutically acceptable excipient, wherein the inflammatory disease or condition is selected from the group consisting of sepsis, trauma, acute pancreatitis, acute respiratory distress syndrome, ischemia-reperfusion injury, cardiovascular disease, toxicity caused by chemotherapy, radiotherapy, or cytokine chemotherapy, burns and tumor metastasis.

2. The method of claim 1, wherein the inflammatory disease or condition involves pro-inflammatory signaling by Toll-like Receptor 2 (TLR2).

3. The method of claim 1, wherein the subject is a mammal.

4. The method of claim 3, wherein the subject is a human.

5. The method of claim 1, wherein administration of the compound inhibits signaling by Toll-like Receptor 2 (TLR2).

6. The method of claim 1, wherein administration of the compound inhibits signaling by Toll-like Receptor 2/Toll-like receptor 1 (TLR2/TLR1) and/or Toll-like receptor 2/Toll-like receptor 6 (TLR2/TLR6).

7. The method of claim 1, wherein administration of the compound inhibits signaling by Toll-like Receptor 2/Toll-like receptor 1 (TLR2/TLR1) to a greater degree than TLR2/TLR6.

8. The method of claim 1, wherein administration of the compound does not inhibit TNF-α-induced signaling.

9. The method of claim 1, wherein the compound is C29 or ortho-vanillin.

10. The method of claim 1, wherein the composition is administered by injection, wherein the composition comprises a pharmaceutically acceptable excipient.

11. A method of treating an inflammatory disease or condition in a subject consisting of administering to the subject a therapeutically effective amount of a compound selected from the group consisting of C29, ortho-vanillin, a salt of C29, a solvate of C29, a hydrate of C29, a prodrug of C29, a salt of ortho-vanillin, a solvate of ortho-vanillin, a hydrate of ortho-vanillin, a prodrug of ortho-vanillin, and a combination thereof, wherein the compound is administered in a composition comprising a pharmaceutically acceptable excipient, wherein the composition is administered by injection, wherein the inflammatory disease or condition is selected from the group consisting of sepsis, trauma, acute pancreatitis, acute respiratory distress syndrome, ischemia-reperfusion injury, cardiovascular disease, toxicity caused by chemotherapy, radiotherapy, or cytokine chemotherapy, burns and tumor metastasis.

12. The method of claim 11, wherein the subject is a human.

13. The method of claim 11, wherein administration of the compound inhibits signaling by Toll-like Receptor 2 (TLR2).

14. The method of claim 11, wherein administration of the compound does not inhibit TNF-α-induced signaling.

15. The method of claim 12, wherein the compound is C29 or ortho-vanillin.

16. The method of claim 1, wherein the compound is C29 or a salt, solvate, hydrate or prodrug thereof.

17. The method of claim 1, wherein the compound is ortho-vanillin or a salt, solvate, hydrate or prodrug thereof.

18. The method of claim 11, wherein the compound is C29 or a salt, solvate, hydrate or prodrug thereof.

19. The method of claim 11, wherein the compound is ortho-vanillin or a salt, solvate, hydrate or prodrug thereof.

* * * * *